US012806331B2

(12) United States Patent
Breingan et al.

(10) Patent No.: US 12,806,331 B2
(45) Date of Patent: Nov. 24, 2026

(54) DRIVE DEVICE INCLUDING FLEXIBLE PLUNGER SHAFT

(71) Applicant: INSULET CORPORATION, Acton, MA (US)

(72) Inventors: Kyle Breingan, Lowell, MA (US); Daniel Barrett, Somerville, MA (US); Lucas Mcgahren, Somerville, MA (US)

(73) Assignee: INSULET CORPORATION, Acton, MA (US)

(*) Notice: Subject to any disclaimer, the term of this patent is extended or adjusted under 35 U.S.C. 154(b) by 870 days.

(21) Appl. No.: 18/164,708

(22) Filed: Feb. 6, 2023

(65) Prior Publication Data

US 2023/0248901 A1 Aug. 10, 2023

Related U.S. Application Data

(60) Provisional application No. 63/308,822, filed on Feb. 10, 2022.

(51) Int. Cl.
*A61M 5/142* (2006.01)

(52) U.S. Cl.
CPC .... *A61M 5/14216* (2013.01); *A61M 5/14244* (2013.01)

(58) Field of Classification Search
CPC ...... A61M 2005/14533; A61M 5/1452; A61M 2005/31518; A61M 5/14216;
(Continued)

(56) References Cited

U.S. PATENT DOCUMENTS 1,441,508 A 1/1923 Jensen
2,198,666 A 4/1940 Gruskin
(Continued)

FOREIGN PATENT DOCUMENTS

CA 606281 A 10/1960
CN 1375338 A 10/2002
(Continued)

OTHER PUBLICATIONS

International Search Report and Written Opinion for PCT/US2018/014351, mailed on Jun. 4, 2018, 9 pages.
(Continued)

*Primary Examiner* — Quynh-Nhu H. Vu
(74) *Attorney, Agent, or Firm* — Goodwin Procter LLP

(57) ABSTRACT

Embodiments of the present disclosure relate to techniques, processes, devices or systems for pump devices. In one approach, a wearable drug delivery device may include a reservoir configured to store a fluid, the reservoir including a housing defining an interior chamber. The wearable drug delivery device may further include a drive device for driving the fluid from the reservoir, the drive device including a plunger head within the interior chamber of the housing, and a plunger shaft extending from the plunger head. The plunger shaft may include a first component adjacent a second component, wherein during movement of the plunger head in a first direction the first and second components engage one another to form a rigid portion of the plunger shaft, and wherein during movement of the plunger head in a second direction, opposite the first direction, the first and second components are separated from one another.

13 Claims, 13 Drawing Sheets

(58) Field of Classification Search
CPC ...... A61M 5/14244; A61M 2005/3152; A61M 5/31511; A61M 5/31526; A61M 5/31573; A61M 5/31575; A61M 5/31576; A61M 5/31583
See application file for complete search history.

(56) References Cited

U.S. PATENT DOCUMENTS 2,752,918 A 7/1956 Uytenbogaar
3,176,712 A 4/1965 Ramsden
3,297,260 A 1/1967 Barlow
3,464,359 A 9/1969 King
3,885,662 A 5/1975 Schaefer
3,946,732 A 3/1976 Hurscham
3,947,692 A 3/1976 Payne
3,993,061 A 11/1976 OLeary
4,108,177 A 8/1978 Pistor
4,152,098 A 5/1979 Moody et al.
4,210,173 A 7/1980 Choksi et al.
4,221,219 A 9/1980 Tucker
4,257,324 A 3/1981 Stefansson et al.
4,268,150 A 5/1981 Chen
4,277,226 A 7/1981 Archibald
4,313,439 A 2/1982 Babb et al.
4,371,790 A 2/1983 Manning et al.
4,417,889 A 11/1983 Choi
4,424,720 A 1/1984 Bucchianeri
4,435,173 A 3/1984 Siposs et al.
4,475,905 A 10/1984 Himmelstrup
4,498,843 A 2/1985 Schneider et al.
4,507,115 A 3/1985 Kambara et al.
4,551,134 A 11/1985 Slavik et al.
4,562,751 A 1/1986 Nason et al.
4,567,549 A 1/1986 Lemme
4,585,439 A 4/1986 Michel
4,601,707 A 7/1986 Albisser et al.
4,634,427 A 1/1987 Hannula et al.
4,671,429 A 6/1987 Spaanderman et al.
4,678,408 A 7/1987 Nason et al.
4,684,368 A 8/1987 Kenyon
4,685,903 A 8/1987 Cable et al.
4,755,169 A 7/1988 Sarnoff et al.
4,766,889 A 8/1988 Trick et al.
4,808,161 A 2/1989 Kamen
4,846,797 A 7/1989 Howson et al.
4,858,619 A 8/1989 Toth
4,898,579 A 2/1990 Groshong et al.
4,908,017 A 3/1990 Howson et al.
4,944,659 A 7/1990 Labbe et al.
4,969,874 A 11/1990 Michel et al.
4,991,743 A 2/1991 Walker
5,007,458 A 4/1991 Marcus et al.
5,020,325 A 6/1991 Henault
5,062,551 A * 11/1991 Goldstein .............. A45D 40/02 222/391
5,062,841 A 11/1991 Siegel
5,147,311 A 9/1992 Pickhard
5,178,609 A 1/1993 Ishikawa
5,205,819 A 4/1993 Ross et al.
5,213,483 A 5/1993 Flaherty et al.
5,222,362 A 6/1993 Maus et al.
5,236,416 A 8/1993 McDaniel et al.
5,261,882 A 11/1993 Sealfon
5,261,884 A 11/1993 Stern et al.
5,277,338 A 1/1994 Divall et al.
5,281,202 A 1/1994 Weber et al.
5,346,476 A 9/1994 Elson
5,364,342 A 11/1994 Beuchat et al.
5,388,615 A 2/1995 Edlund et al.
5,433,710 A 7/1995 VanAntwerp et al.
5,503,628 A 4/1996 Fetters et al.
5,520,661 A 5/1996 Lal et al.
5,533,389 A 7/1996 Kamen et al.
5,582,593 A 12/1996 Hultman
5,618,269 A 4/1997 Jacobsen et al.
5,628,309 A 5/1997 Brown
5,637,095 A 6/1997 Nason et al.
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,839,467 A 11/1998 Saaski et al.
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
5,971,963 A 10/1999 Choi
6,019,747 A 2/2000 McPhee
6,050,457 A 4/2000 Arnold et al.
6,068,615 A 5/2000 Brown et al.
6,159,188 A 12/2000 Laibovitz et al.
6,174,300 B1 1/2001 Kriesel et al.
6,190,359 B1 2/2001 Heruth
6,200,293 B1 3/2001 Kriesel et al.
6,352,522 B1 3/2002 Kim et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,183 B1 * 12/2002 Braeuninger-Weimer .................. A61M 5/3158 222/326
6,488,652 B1 12/2002 Weijand et al.
6,520,936 B1 2/2003 Mann
6,527,744 B1 3/2003 Kriesel et al.
6,537,249 B2 3/2003 Kriesell et al.
6,537,251 B2 * 3/2003 Klitmose .......... A61M 5/14566 604/131
6,539,286 B1 3/2003 Jiang
6,569,115 B1 5/2003 Barker et al.
6,595,956 B1 7/2003 Gross et al.
6,656,158 B2 12/2003 Mahoney et al.
6,699,218 B2 3/2004 Flaherty et al.
6,723,072 B2 4/2004 Flaherty et al.
6,740,059 B2 5/2004 Flaherty
6,749,407 B2 6/2004 Xie et al.
6,851,260 B2 2/2005 Mernoe
6,883,778 B1 4/2005 Newton et al.
7,018,360 B2 3/2006 Flaherty et al.
7,104,275 B2 9/2006 Dille
7,128,727 B2 10/2006 Flaherty et al.
7,137,964 B2 11/2006 Flaherty
7,160,272 B1 1/2007 Eyal et al.
7,303,549 B2 12/2007 Flaherty
7,699,833 B2 * 4/2010 Moberg .............. A61M 5/1413 604/890.1
7,771,392 B2 8/2010 De Polo et al.
7,914,499 B2 3/2011 Gonnelli et al.
7,951,114 B2 5/2011 Rush et al.
8,267,921 B2 9/2012 Yodfat et al.
8,382,703 B1 2/2013 Abdelaal
8,499,913 B2 8/2013 Gunter
8,905,995 B2 12/2014 Mernoe
8,920,376 B2 12/2014 Caffey et al.
8,939,935 B2 1/2015 OConnor et al.
9,180,244 B2 11/2015 Anderson et al.
9,192,716 B2 11/2015 Jugl et al.
9,402,950 B2 8/2016 Dilanni et al.
9,539,596 B2 1/2017 Ikushima
10,441,723 B2 10/2019 Nazzaro
10,695,485 B2 6/2020 Nazzaro
2001/0016710 A1 8/2001 Nason et al.
2001/0056258 A1 12/2001 Evans
2002/0029018 A1 3/2002 Jeffrey

(56) References Cited

U.S. PATENT DOCUMENTS

| | | | |
|---|---|---|---|
| 2002/0032374 | A1 | 3/2002 | Holker et al. |
| 2002/0037221 | A1 | 3/2002 | Mastrangelo et al. |
| 2002/0173769 | A1 | 11/2002 | Gray et al. |
| 2002/0173830 | A1 | 11/2002 | Starkweather et al. |
| 2003/0040715 | A1 | 2/2003 | DAntonio et al. |
| 2003/0055380 | A1 | 3/2003 | Flaherty |
| 2003/0097092 | A1 | 5/2003 | Flaherty |
| 2003/0109827 | A1 | 6/2003 | Lavi et al. |
| 2003/0163097 | A1 | 8/2003 | Fleury et al. |
| 2003/0198558 | A1 | 10/2003 | Nason et al. |
| 2003/0199825 | A1 | 10/2003 | Flaherty |
| 2004/0010207 | A1 | 1/2004 | Flaherty et al. |
| 2004/0064088 | A1 | 4/2004 | Gorman et al. |
| 2004/0068224 | A1 | 4/2004 | Couvillon, Jr. et al. |
| 2004/0069044 | A1 | 4/2004 | Lavi et al. |
| 2004/0092865 | A1 | 5/2004 | Flaherty et al. |
| 2004/0094733 | A1 | 5/2004 | Hower et al. |
| 2004/0153032 | A1 | 8/2004 | Garribotto et al. |
| 2005/0020980 | A1 | 1/2005 | Inoue et al. |
| 2005/0165363 | A1 | 7/2005 | Judson et al. |
| 2005/0203461 | A1 | 9/2005 | Flaherty et al. |
| 2005/0238507 | A1 | 10/2005 | Dilanni et al. |
| 2005/0273059 | A1 | 12/2005 | Mernoe |
| 2005/0277882 | A1 | 12/2005 | Kriesel |
| 2006/0041229 | A1 | 2/2006 | Garibotto et al. |
| 2006/0079765 | A1 | 4/2006 | Neer et al. |
| 2006/0155210 | A1 | 7/2006 | Beckman et al. |
| 2006/0173439 | A1 | 8/2006 | Thorne et al. |
| 2006/0178633 | A1 | 8/2006 | Garibotto et al. |
| 2006/0253085 | A1 | 11/2006 | Geismar et al. |
| 2006/0282290 | A1 | 12/2006 | Flaherty et al. |
| 2007/0005018 | A1 | 1/2007 | Tekbuchava |
| 2007/0073236 | A1 | 3/2007 | Merno et al. |
| 2007/0088271 | A1 | 4/2007 | Richards |
| 2007/0118405 | A1 | 5/2007 | Campbell et al. |
| 2007/0282269 | A1 | 12/2007 | Carter et al. |
| 2008/0004515 | A1 | 1/2008 | Jennewine |
| 2008/0051738 | A1 | 2/2008 | Griffin |
| 2008/0114304 | A1 | 5/2008 | Nalesso et al. |
| 2008/0172028 | A1 | 7/2008 | Blomquist |
| 2008/0243211 | A1 | 10/2008 | Cartwright et al. |
| 2008/0294040 | A1 | 11/2008 | Mohiuddin et al. |
| 2009/0024083 | A1 | 1/2009 | Kriesel et al. |
| 2009/0062767 | A1 | 3/2009 | Van Antwerp et al. |
| 2009/0198215 | A1 | 8/2009 | Chong et al. |
| 2009/0278875 | A1 | 11/2009 | Holm et al. |
| 2009/0326472 | A1 | 12/2009 | Carter et al. |
| 2010/0036326 | A1 | 2/2010 | Matusch |
| 2010/0152658 | A1 | 6/2010 | Hanson et al. |
| 2010/0241066 | A1 | 9/2010 | Hansen et al. |
| 2011/0054399 | A1 | 3/2011 | Chong et al. |
| 2011/0073620 | A1 | 3/2011 | Verrilli |
| 2011/0144586 | A1 | 6/2011 | Michaud et al. |
| 2011/0180480 | A1 | 7/2011 | Kloeffel et al. |
| 2011/0230833 | A1 | 9/2011 | Landman et al. |
| 2012/0078161 | A1 | 3/2012 | Masterson et al. |
| 2012/0172817 | A1 | 7/2012 | Bruggemann et al. |
| 2012/0209207 | A1 | 8/2012 | Gray et al. |
| 2013/0006213 | A1 | 1/2013 | Arnitz et al. |
| 2013/0017099 | A1 | 1/2013 | Genoud |
| 2013/0064701 | A1 | 3/2013 | Konishi |
| 2013/0177455 | A1 | 7/2013 | Kamen et al. |
| 2013/0178803 | A1 | 7/2013 | Raab |
| 2013/0245545 | A1 | 9/2013 | Arnold et al. |
| 2013/0267932 | A1 | 10/2013 | Franke et al. |
| 2013/0296792 | A1 | 11/2013 | Cabiri |
| 2014/0018730 | A1 | 1/2014 | Muller-Pathle |
| 2014/0127048 | A1 | 5/2014 | Dilanni et al. |
| 2014/0128839 | A1 | 5/2014 | Dilanni et al. |
| 2014/0142508 | A1 | 5/2014 | Dilanni et al. |
| 2014/0148784 | A1 | 5/2014 | Anderson et al. |
| 2014/0171901 | A1 | 6/2014 | Langsdorf et al. |
| 2015/0041498 | A1 | 2/2015 | Kakiuchi et al. |
| 2015/0051487 | A1 | 2/2015 | Uber et al. |
| 2015/0057613 | A1 | 2/2015 | Clemente et al. |
| 2015/0064036 | A1 | 3/2015 | Eberhard |
| 2015/0137017 | A1 | 5/2015 | Ambrosina et al. |
| 2015/0202386 | A1 | 7/2015 | Brady et al. |
| 2015/0290389 | A1 | 10/2015 | Nessel |
| 2015/0290392 | A1* | 10/2015 | Henderson ............ A61M 5/283 604/116 |
| 2015/0297825 | A1 | 10/2015 | Focht et al. |
| 2016/0008549 | A1 | 1/2016 | Plumptre et al. |
| 2016/0025544 | A1 | 1/2016 | Kamen |
| 2016/0055842 | A1 | 2/2016 | Defranks et al. |
| 2016/0082242 | A1 | 3/2016 | Burton et al. |
| 2016/0129190 | A1 | 5/2016 | Haitsuka |
| 2016/0193423 | A1 | 7/2016 | Bilton |
| 2016/0213851 | A1 | 7/2016 | Weibel et al. |
| 2017/0021096 | A1 | 1/2017 | Cole et al. |
| 2017/0021137 | A1 | 1/2017 | Cole |
| 2017/0049968 | A1* | 2/2017 | Choi ....................... A61M 5/20 |
| 2017/0100541 | A1 | 4/2017 | Constantineau et al. |
| 2017/0216516 | A1 | 8/2017 | Dale |
| 2017/0239415 | A1 | 8/2017 | Hwang et al. |
| 2017/0290975 | A1 | 10/2017 | Barmaimon et al. |
| 2018/0021521 | A1 | 1/2018 | Sanchez |
| 2018/0185579 | A1 | 7/2018 | Joseph et al. |
| 2018/0313346 | A1 | 11/2018 | Oakes |
| 2019/0192782 | A1 | 6/2019 | Pedersen et al. |
| 2019/0365993 | A1 | 12/2019 | Staub et al. |
| 2020/0009315 | A1 | 1/2020 | Brouet et al. |
| 2020/0345931 | A1 | 11/2020 | Gray et al. |
| 2024/0358929 | A1* | 10/2024 | Chang ................ A61M 5/31511 |

FOREIGN PATENT DOCUMENTS

| | | | |
|---|---|---|---|
| CN | 102498292 | B | 7/2015 |
| CN | 204972511 | U | 1/2016 |
| CN | 105764543 | B | 7/2016 |
| CN | 206175149 | U | 5/2017 |
| CN | 107096091 | A | 8/2017 |
| CN | 108472441 | A | 8/2018 |
| DE | 4200595 | A1 | 7/1993 |
| DE | 19723648 | C1 | 8/1998 |
| DE | 102005040344 | A1 | 3/2007 |
| EP | 0454331 | A1 | 10/1991 |
| EP | 0789146 | A1 | 8/1997 |
| EP | 867196 | A2 | 9/1998 |
| EP | 1065378 | A2 | 1/2001 |
| EP | 1177802 | A1 | 2/2002 |
| EP | 1202917 | B1 | 4/2003 |
| EP | 1403519 | A1 | 3/2004 |
| EP | 2397181 | A1 | 12/2011 |
| EP | 2468338 | A1 | 6/2012 |
| EP | 2703024 | A1 | 3/2014 |
| EP | 1874390 | B1 | 10/2014 |
| EP | 2830499 | A1 | 2/2015 |
| EP | 3260147 | A1 | 12/2017 |
| FR | 2096275 | A5 | 2/1972 |
| FR | 2455269 | A1 | 11/1980 |
| FR | 2507637 | A1 | 12/1982 |
| FR | 2731475 | A1 | 9/1996 |
| GB | 357139 | A | 9/1931 |
| GB | B10488 | A | 3/1959 |
| GB | 875034 | A | 8/1961 |
| GB | 1204836 | A | 9/1970 |
| GB | 2008806 | A | 6/1979 |
| GB | 2077367 | A | 12/1981 |
| GB | 2456681 | A | 7/2009 |
| GB | 2549750 | A | 11/2017 |
| IL | 46017 | A | 11/1977 |
| JP | 06063133 | A | 3/1994 |
| JP | H06296690 | A | 10/1994 |
| JP | H08238324 | A | 9/1996 |
| JP | 2004247271 | A | 9/2004 |
| JP | 2004274719 | A | 9/2004 |
| JP | 2005188355 | A | 7/2005 |
| JP | 2006159228 | A | 6/2006 |
| JP | 6098988 | B2 | 9/2006 |
| JP | 2006249130 | A | 9/2006 |
| JP | 2009514580 | A | 4/2009 |
| JP | 2017513577 | A | 6/2017 |
| NL | 1019126 | C1 | 4/2003 |

(56) References Cited

FOREIGN PATENT DOCUMENTS

| | | | | |
|---|---|---|---|---|
| WO | 8101658 A1 | 6/1981 | | |
| WO | 8606796 A1 | 11/1986 | | |
| WO | 9320864 A1 | 10/1993 | | |
| WO | 9415660 A1 | 7/1994 | | |
| WO | 9855073 A1 | 12/1998 | | |
| WO | 9856293 A1 | 12/1998 | | |
| WO | 9910040 A1 | 3/1999 | | |
| WO | 9910049 A1 | 3/1999 | | |
| WO | 9962576 A1 | 12/1999 | | |
| WO | 0029047 A1 | 5/2000 | | |
| WO | 0178812 A1 | 10/2001 | | |
| WO | 0220073 A2 | 3/2002 | | |
| WO | 0226282 A2 | 4/2002 | | |
| WO | 2002076535 A1 | 4/2002 | | |
| WO | 2003097133 A1 | 4/2002 | | |
| WO | 02068823 A1 | 9/2002 | | |
| WO | 2004032994 A2 | 4/2004 | | |
| WO | 2004056412 A2 | 7/2004 | | |
| WO | 2004110526 A1 | 12/2004 | | |
| WO | 2007066152 A2 | 6/2007 | | |
| WO | 2008133702 A1 | 11/2008 | | |
| WO | 2009039203 A2 | 3/2009 | | |
| WO | 2009141005 A1 | 11/2009 | | |
| WO | 2010022069 A2 | 2/2010 | | |
| WO | 2010077279 A1 | 7/2010 | | |
| WO | 2010139793 A1 | 12/2010 | | |
| WO | 2011010198 A2 | 1/2011 | | |
| WO | 2011031458 A1 | 3/2011 | | |
| WO | 2011069935 A2 | 6/2011 | | |
| WO | 2011075042 A1 | 6/2011 | | |
| WO | 2011133823 A1 | 10/2011 | | |
| WO | WO-2012056265 A1 * | 5/2012 | ........ | A61M 5/31511 |
| WO | 2012073032 A1 | 6/2012 | | |
| WO | 2013050535 A2 | 4/2013 | | |
| WO | 2013137893 A1 | 9/2013 | | |
| WO | 2013149186 A1 | 10/2013 | | |
| WO | 2014029416 A1 | 2/2014 | | |
| WO | 2014149357 A1 | 9/2014 | | |
| WO | 2014179774 A1 | 11/2014 | | |
| WO | 2015032772 A1 | 3/2015 | | |
| WO | 2015048791 A1 | 4/2015 | | |
| WO | 2015081337 A2 | 6/2015 | | |
| WO | 2015117854 A1 | 8/2015 | | |
| WO | 2015167201 A1 | 11/2015 | | |
| WO | 2015177082 A1 | 11/2015 | | |
| WO | 2017148855 A1 | 9/2017 | | |
| WO | 2017187177 A1 | 11/2017 | | |
| WO | 2021016452 A1 | 1/2021 | | |
| WO | 2023030877 A1 | 3/2023 | | |

OTHER PUBLICATIONS

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin bumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962-972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

European Search Report and Written Opinion for the European Patent Application No. EP19177571, dated Oct. 30, 2019, 8 pages.

International Preliminary Report on Patentability for International Patent Application No. PCT/US2018/014351, dated Jul. 23, 2019, 7 pages.

International Preliminary Report on Patentability for International Patent Application No. PCT/US2017/046777, dated Feb. 19, 2019, 8 pages.

International Preliminary Report on Patentability for International Patent Application No. PCT/US2017/046737, dated Feb. 19, 2019, 8 pages.

International Preliminary Report on Patentability for International Patent Application No. PCT/US2017/055054, dated Apr. 9, 2019, 8 pages.

International Search Report and Written Opinion for Application No. PCT/US2017/034811, mailed Oct. 18, 2017, 15 pages.

EPO Search Report received in Application No. 13768938.6, dated Nov. 11, 2015, 8 pages.

International Search Report and Written Opinion for PCT Application No. PCT/US13/34674, mailed Aug. 6, 2013, 17 pages.

International Search Report and Written Opinion for International Application No. PCT/GB2007/004073, Jan. 31, 2008, 8 pages.

International Search Report and Written Opinion for International Patent Application No. PCT/US2019/063615, dated May 3, 2020, 17 pages.

International Preliminary Report on Patentability for International Patent Application No. PCT/US2018/045155, dated Feb. 14, 2020, 10 pages.

International Search Report and Written Opinion for International Patent Application No. PCT/US2019/035756, dated Jul. 31, 2019, 11 pages.

International Search Report and Written Opinion for PCT Application No. PCT/US2019/059854, mailed Aug. 26, 2020, 15 pages.

International Search Report and Written Opinion, Application No. PCT/US2022/016713, mailed Aug. 5, 2022, 19 pages.

International Search Report and Written Opinion for International Patent Application No. PCT/US2022/029012, mailed Aug. 19, 2022, 12 pages.

European Search Report and Written Opinion for European Patent Application No. EP20174878, dated Sep. 29, 2020, 8 pages.

Schott web-page image from Jul. 9, 2016, https://www.us.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

(56) References Cited

OTHER PUBLICATIONS

International Search Report and Written Opinion for International Patent Application No. PCT/US2023/062014, dated May 22, 2023, 11 pages.

* cited by examiner

DRIVE DEVICE INCLUDING FLEXIBLE PLUNGER SHAFT

RELATED APPLICATIONS

This application claims the benefit of U.S. Provisional Patent Application No. 63/308,822, filed Feb. 10, 2022, the contents of which are incorporated herein by reference in their entirety.

TECHNICAL FIELD

The disclosed embodiments generally relate to medication delivery. More particularly, the disclosed embodiments relate to techniques, processes, systems, and dispensing devices for delivering a fluid medicament in a space-efficient manner using a flexible plunger shaft.

BACKGROUND

Fluid delivery devices have numerous uses such as delivering a fluid medicament to a patient subcutaneously. In a patient with diabetes mellitus, for example, ambulatory infusion pumps have been used to deliver insulin to the patient. These infusion pumps have the ability to offer sophisticated fluid delivery profiles including variable basal rates and bolus requirements. The ability to carefully control drug delivery can result in better efficacy of the drug and therapy and less toxicity to the patient.

Some existing infusion pumps include a reservoir to contain the fluid medicament and use electromechanical pumping or metering technology to deliver the fluid medicament via tubing to a needle and/or soft cannula that is inserted subcutaneously into the patient. Some infusion pumps have been designed to be relatively small, low cost, light-weight, and easy-to-use. These pumps include a drive mechanism having a leadscrew extending from a plunger. The leadscrew and plunger convert the rotational motion of an actuator, which may be one or more SMA wires, solenoids, motors, etc., to an accurate linear motion. The design of the drive mechanism may be improved, however, to reduce the size of the pump, to improve the comfort to the user, and/or to reduce the number of components of the pump.

Accordingly, there is a need for a simplified system for accurately expelling fluid medicament from a reservoir, which also reduces overall drug delivery device size.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a reservoir configured to store a fluid, the reservoir including a housing defining an interior chamber. The wearable drug delivery device may further include a drive device for driving the fluid from the reservoir, the drive device including a plunger head within the interior chamber of the housing, and a plunger shaft extending from the plunger head. The plunger shaft may include a first component adjacent a second component, wherein during movement of the plunger head in a first direction the first and second components engage one another to form a rigid portion of the plunger shaft.

In some approaches, a drive device of a wearable drug delivery device may include a plunger head in contact with an interior surface of a housing of a reservoir, the reservoir configured to store a fluid, and a plunger shaft extending from the plunger head. The plunger shaft may include a first component adjacent a second component, wherein during movement of the plunger head in a first direction the first and second components engage with one another to form a rigid portion of the plunger shaft, and wherein during movement of the plunger head in a second direction, opposite the first direction, the first and second components are moved away from one another.

In some approaches, a method may include providing a reservoir configured to store a liquid drug, the reservoir comprising a housing including a wall defining an interior chamber, and positioning a drive device within the interior chamber of the housing. The drive device may include a plunger head within the interior chamber of the housing, and a plunger shaft including a first component adjacent a second component, wherein a first end of the first and second components is coupled to the plunger head, and wherein a second end of the first and second components extends outside of the housing of the reservoir. The method may further include biasing the plunger head between a first position and a second position within the housing to modify a volume of the liquid drug, wherein in the first position the first end of the first and second components are engaged together to increase rigidity of the plunger shaft, and wherein in the second position the first and second components are separated from one another to decrease rigidity of the plunger shaft.

BRIEF DESCRIPTION OF THE DRAWINGS

In the drawings, like reference characters generally refer to the same parts throughout the different views. In the following description, various embodiments of the present disclosure are described with reference to the following drawings, in which.

The drawings are not necessarily to scale. The drawings are merely representations, not intended to portray specific parameters of the disclosure. The drawings are intended to depict exemplary embodiments of the disclosure, and therefore are not to be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

As noted above, existing pumps often include a leadscrew positioned within and/or behind a reservoir. A main drawback of this type of drive mechanism is leadscrew length. To provide a reduced-size pump, which increases user comfort, embodiments of the present disclosure replace the leadscrew with a flexible plunger shaft, which allows for increased reservoir volume while further reducing in size or maintaining an overall compact design. More specifically, in some embodiments, a flexible zipper-like leadscrew replacement allows the drive system to flex or bend out of the way when the reservoir is full, and to transition into a rigid drive shaft while a fluid is being delivered from the reservoir. The rigid portion of the plunger shaft may be created by interlocking two flexible members together, wherein each of the flexible members are weak in opposite directions (relative to the other flexible member), allowing them to bend before zipping together and forming the rigid portion. In some embodiments, the flexible members may be driven by a pinion or gear-like rotary drive.

In various embodiments, the wearable drug delivery device described herein may include an analyte sensor, such as a blood glucose sensor, and the cannula or microneedle array may be operable in allowing the device to measure an analyte level in a user of the device, in addition to delivering a liquid drug.

Figure 1:
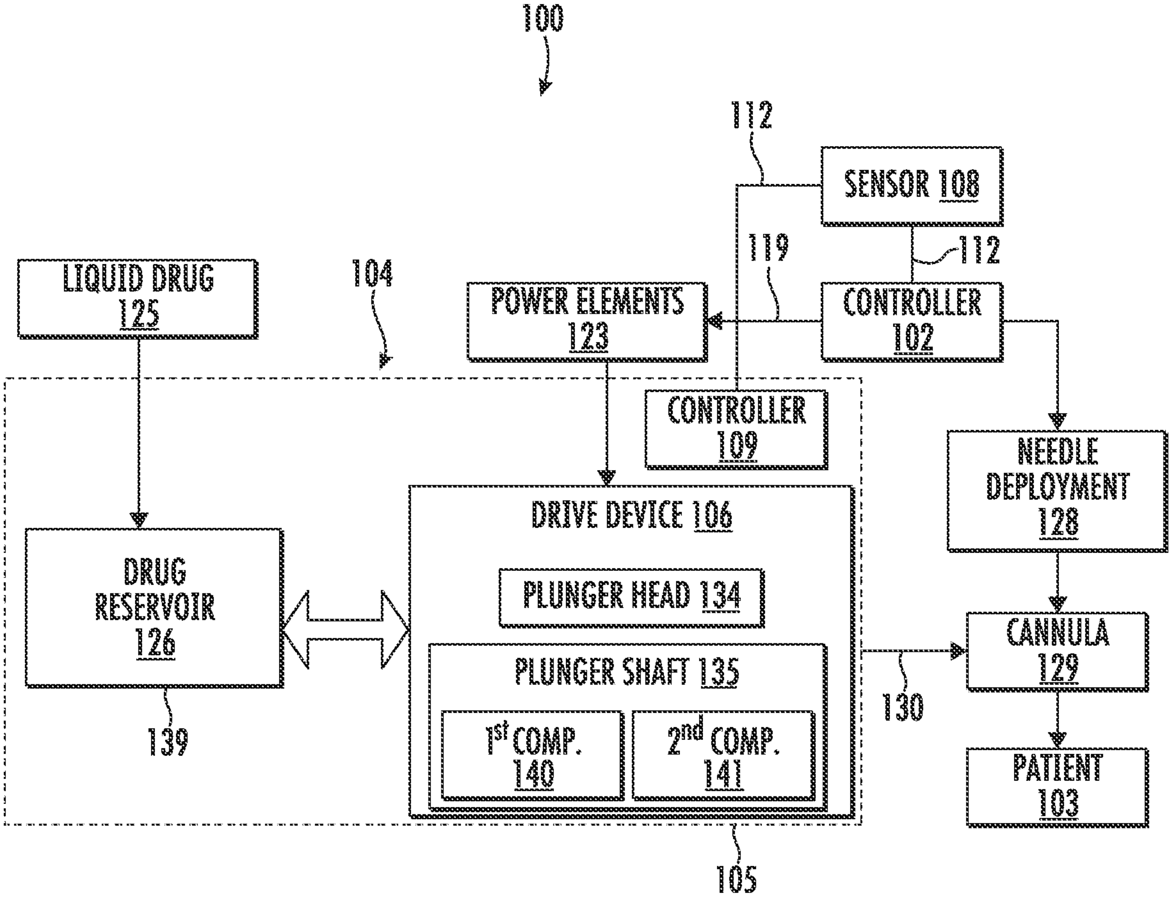
FIG. 1 illustrates a schematic diagram of a drug delivery system according to embodiments of the present disclosure.

FIG. 1 illustrates a simplified block diagram of an example system (hereinafter "system") 100. The system 100 may be a wearable or on-body drug delivery device and/or an analyte sensor attached to the skin of a patient 103. The system 100 may include a controller 102, a pump mechanism 104 (hereinafter "pump 104"), and a sensor 108 within one or more housings. The sensor 108 may be a glucose or other analyte monitor such as, for example, a continuous glucose monitor, and may be incorporated into the wearable device. The sensor 108 may, for example, be operable to measure blood glucose (BG) values of a user to generate a measured BG level signal 112. The controller 102, the pump 104, and the sensor 108 may be communicatively coupled to one another via a wired or wireless communication path. For example, each of the controller 102, the pump 104 and the sensor 108 may be equipped with a wireless radio frequency transceiver operable to communicate via one or more communication protocols, such as Bluetooth®, or the like.

The system 100 may further include a delivery pump device (hereinafter "device") 105, which includes a drive device 106 coupled to a reservoir 126 for driving a liquid drug 125 therefrom. The drive device 106 may further include a piston having a plunger head 134 and a plunger shaft 135 disposed within an interior chamber of a housing 139 of the reservoir 126. As will be described in greater detail herein, the plunger shaft 135 may be a flexible shaft including a first component 140 and a second component 141, which may be biased in first direction to engage one another to form a rigid portion of the plunger shaft 135. As explained herein, first component 140 and second component 141 may be flexible members, at least in one direction (which may allow each component to coil around itself), but may be unbendable in a second direction, and when first and second components 140, 141 engage or mate with each other, the combined structure forms a rigid portion of plunger shaft 135. When the plunger shaft 135 is moved in a second direction, opposite the first direction, the first and second components separate from one another and then fold, bend, and/or coil into an alternative configuration. The system 100 may include additional components which are not shown or described for the sake of brevity.

The controller 102 may receive a desired BG level signal, which may be a first signal, indicating a desired BG level or range for the patient 103. The desired BG level signal may be stored in memory of a controller 109 on device 105, received from a user interface to the controller 102, or another device, or by an algorithm within controller 109 (or controller 102) that automatically determines an appropriate BG level or target for the patient 103. The sensor 108 may be coupled to the patient 103 and operable to measure an approximate value of a BG level of the user. In response to the measured BG level or value, the sensor 108 may generate a signal indicating the measured BG value. As shown, the controller 102 may also receive from the sensor 108 via a communication path, the measured BG level signal 112, which may be a second signal.

Based on the desired BG level signal and the measured BG level signal 112, the controller 102 or controller 109 may generate one or more control signals for directing operation of the pump 104. For example, one control signal 119 from the controller 102 or controller 109 may cause the pump 104 to turn on, or activate one or more power elements 123 operably connected with the device 105. The specified amount of the liquid drug 125 may be determined as an appropriate amount of insulin to drive the measured BG level of the user to the desired BG level. Based on operation of the pump 104, as determined by the control signal 119, the patient 103 may receive the liquid drug from the reservoir 126. The system 100 may operate as a closed-loop system, an open-loop system, or as a hybrid system. In an exemplary closed-loop system, the controller 109 may direct operation of the device 105 without input from the controller 102, and may receive BG level signal 112 from the sensor 108. The sensor 108 may be housed within the device 105 or may be housed in a separate device and communicate wirelessly directly with the device 105.

As further shown, the system 100 may include a needle deployment component 128 that is in communication with the controller 102 or the controller 109. The needle deployment component 128 may include a needle/cannula 129 deployable into the patient 103 and may have one or more holes at a distal end thereof. The needle deployment component 128 may be housed within the device 105 or a separate component connectable to the device 105. The device 105 may be connected to the needle/cannula 129 by a fluid path component 130. The fluid path component 130 may be of any size and shape and may be made from any material. The fluid path component 130 can allow fluid, such as the liquid drug 125 in the reservoir 126, to be transferred to the needle/cannula 129.

The controller 102/109 may be implemented in hardware, software, or any combination thereof. The controller 102/109 may, for example, be a processor, a logic circuit or a microcontroller coupled to a memory. The controller 102/109 may maintain a date and time as well as other functions (e.g., calculations or the like) performed by processors. The controller 102/109 may be operable to execute an artificial pancreas (AP) algorithm stored in memory (not shown) that enables the controller 102/109 to direct operation of the pump 104. For example, the controller 102/109 may be operable to receive an input from the sensor 108, wherein the input indicates an automated insulin delivery (AID) application setting. Based on the AID application setting, the controller 102/109 may modify the behavior of the pump 104 and resulting amount of the liquid drug 125 to be delivered to the patient 103 via the device 105.

In some embodiments, the sensor 108 may be, for example, a continuous glucose monitor (CGM). The sensor 108 may be physically separate from the pump 104, or may be an integrated component within a same housing thereof or otherwise physically integrated. The sensor 108 may provide the controller 102 with data indicative of measured or detected blood glucose levels of the user.

The power element 123 may be a battery, a piezoelectric device, or the like, for supplying electrical power to the device 105. In other embodiments, the power element 123, or an additional power source (not shown), may also supply power to other components of the pump 104, such as the controller 102, memory, the sensor 108, and/or the needle deployment component 128.

In an example, the sensor 108 may be a device communicatively coupled to the controller 102 and may be operable to measure a blood glucose value at a predetermined time interval, such as approximately every 5 minutes, 10 minutes, or the like. The sensor 108 may provide a number of blood glucose measurement values to the AP application.

In some embodiments, the pump 104, when operating in a normal mode of operation, provides insulin stored in the reservoir 126 to the patient 103 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 108 or other functional elements of the pump 104. For example, the pump 104 may contain analog and/or digital circuitry that may be implemented as the controller 102/109 for controlling the delivery of the drug or therapeutic agent. The circuitry used to implement the controller 102/109 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 102/109 may execute a control algorithm and other programming code that may make the controller 102/109 operable to cause the pump to deliver doses of the drug or therapeutic agent to a user at predetermined intervals or as needed to bring blood glucose measurement values to a target blood glucose value. The size and/or timing of the doses may be at least partially pre-programmed, for example, into the AP application by the patient 103 or by a third party (such as a health care provider, a parent or guardian, a manufacturer of the wearable drug delivery device, or the like) using a wired or wireless link.

Although not shown, in some embodiments, the sensor 108 may include a processor, memory, a sensing or measuring device, and a communication device. The memory may store an instance of an AP application as well as other programming code and be operable to store data related to the AP application.

In various embodiments, the sensing/measuring device of the sensor 108 may include one or more sensing elements, such as a blood glucose measurement element, a blood pressure monitor, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

Turning now to FIG. 2, an example drive device 206 operating with a reservoir 226 of a device 205 according to embodiments of the present disclosure will be described. As shown, the drive device 206 may be positioned partially within an interior chamber 250 of a housing 239 of the reservoir 226. The housing 239 may include a wall 268 including an exterior surface 269 opposite an interior surface 270, the interior surface 270 defining the interior chamber 250. Although non-limiting, the housing 239 may be a circular or an oval-shaped cylinder including a first end 257 opposite a second end 258.

The drive device 206 may include a plunger head 234 disposed within the interior chamber 250 of the housing 239. In some embodiments, the plunger head 234 may include a sealing ring 262 (e.g., O-ring) extending circumferentially about an outer surface of the plunger head 234. The sealing ring 262 may be in direct contact with the interior surface 270 of the wall 268 of the housing 239 to create a liquid-tight seal therebetween.

The drive device 206 may further include a plunger shaft 235 including a first component 240 coupleable with a second component 241 to bias the plunger head 234 between the first end 257 and the second end 258 of the reservoir 226. A first end 238 of the first and second components 240, 241 may be directly coupled to a plunger plate 237, which is secured to the plunger head 234. As shown, the plunger plate 237 may generally extend to the interior surface 270 of the wall 268. In other embodiments, no plunger plate is present, and the first and second components 240, 241 may be directly coupled to the plunger head 234. Embodiments herein are not limited in this context. A second end 236 of the first and second components 240, 241 may extend outside of the housing 239. As will be described in greater detail herein, the second end 236 of each of the first and second components 240, 241 may wrap around opposite sides of the second end 258 of the reservoir 226 and extend along the exterior surface 269 of the wall 268.

As shown, the first component 240 may include a first plurality of protrusions 243 extending outwardly from a first strip of material 285 (e.g., polymer or metal), and a first plurality of indentations 244 extending into the first strip of material 285. Similarly, the second component 241 may include a second plurality of protrusions 245 extending outwardly from a second strip of material 247 (e.g., polymer or metal), and a second plurality of indentations 246 extending into the second strip of material 247. In some embodiments, the first and second plurality of indentations 244, 246 may be openings extending entirely through the first strip of material 285 and the second strip of material 247, respectively. In other embodiments, the first and second plurality of indentations 244, 246 extend only partially through the first strip of material 285 and the second strip of material 247, respectively. In still other embodiments, the first and second plurality of indentations 244, 246 may be defined by the sidewalls of the first plurality of protrusions 243 and the second plurality of protrusions 245, respectively. That is, the first and second plurality of protrusions 243, 254 may be complimentarily shaped to mesh or intertwine with one another.

When the first and second components 240, 241 are brought together, the first plurality of protrusions 243 are operable to engage and interlock with the second plurality of indentations 246. Similarly, the second plurality of protrusions 245 are operable to engage and interlock with the first plurality of indentations 244. Coupling the first and second components 240, 241 together creates a rigid portion 275 of a plunger shaft 235, which helps drive the plunger head 234 towards the first end 257 of the reservoir 226. Prior to being joined, each of the first and second components 240, 241 may be relatively flexible such that each of the first and second components 240, 241 may wrap around the second end 258 of the reservoir 226 and extend substantially parallel to the exterior surface 269 of the wall 268.

In some embodiments, the drive device 206 may further include a plunger shaft housing (hereinafter "housing") 276 operable to contain, guide, and separate the first and second components 240, 241 of the plunger shaft 235. As shown, the housing 276 may include a sidewall 277 extending substantially parallel to the wall 268 of the reservoir 226, and an end wall 278 connected to the sidewall 277. The sidewall 277 and the wall 268 of the reservoir 226 may define a channel 291 for containing and guiding the second end 236 of each of the first and second components 240, 241. In some embodiments, the end wall 278 may include a first curved interior surface 279 operable to bend the first component 240 as the first component 240 moves in and out of the reservoir 226. As shown, the first plurality of protrusions 243 may extend into a first channel 293 defined in part by the first curved interior surface 279, wherein the first channel 293 may guide the first component 240 as it bends around the second end 258 of the reservoir 226. Similarly, the end wall 278 may further include a second curved interior surface 280 operable to bend the second component 241 as the second component 241 moves in and out of the reservoir 226. As shown, the second plurality of protrusions 245 may extend into a second channel 294 defined in part by the second curved interior surface 280, wherein the second channel 294 may guide the second component 241 as it bends around the second end 258 of the reservoir 226. In some embodiments, each of the first and second components 240, 241 may be driven at the respective curves by a gear-like rotary drive (not shown). In other embodiments, the first and second components 240, 241 may be driven by a leadscrew or rack and pinion drive connected to the second end 236 of each of the first and second components 240, 241. Embodiments herein are not limited in this context.

As further shown, the housing 276 may include a crest or wedge 282 operable to separate the first and second components 240, 241 from one another as the plunger head 234 moves towards the second end 258 of the reservoir 226. For example, as the reservoir 226 is filled with the liquid drug 125 (FIG. 1), the plunger head 234 and the rigid portion 275 of the plunger shaft 235 are forced towards the end wall 278. In some embodiments, the driving device, e.g., rotary drive and/or rack and pinion drive, may simulataneously pull the first and second components 240, 241 out of the reservoir 226. As the first and second components 240, 241 are forced against the wedge 282, the first plurality of protrusions 243 become disengaged from the second plurality of indentations 246. Similarly, the second plurality of protrusions 245 become disengaged from the first plurality of indentations 244. Decoupling the first and second components 240, 241 from one another eliminates, or shortens, the rigid portion 275 of the plunger shaft 235, and enables the first and second components 240, 241 to transition from a combined rigid state to a relatively flexible state, which allows each of the first and second components 240, 241 to conform to respective first and second curved interior surfaces 279, 280 of the end wall 278.

Figure 2A:
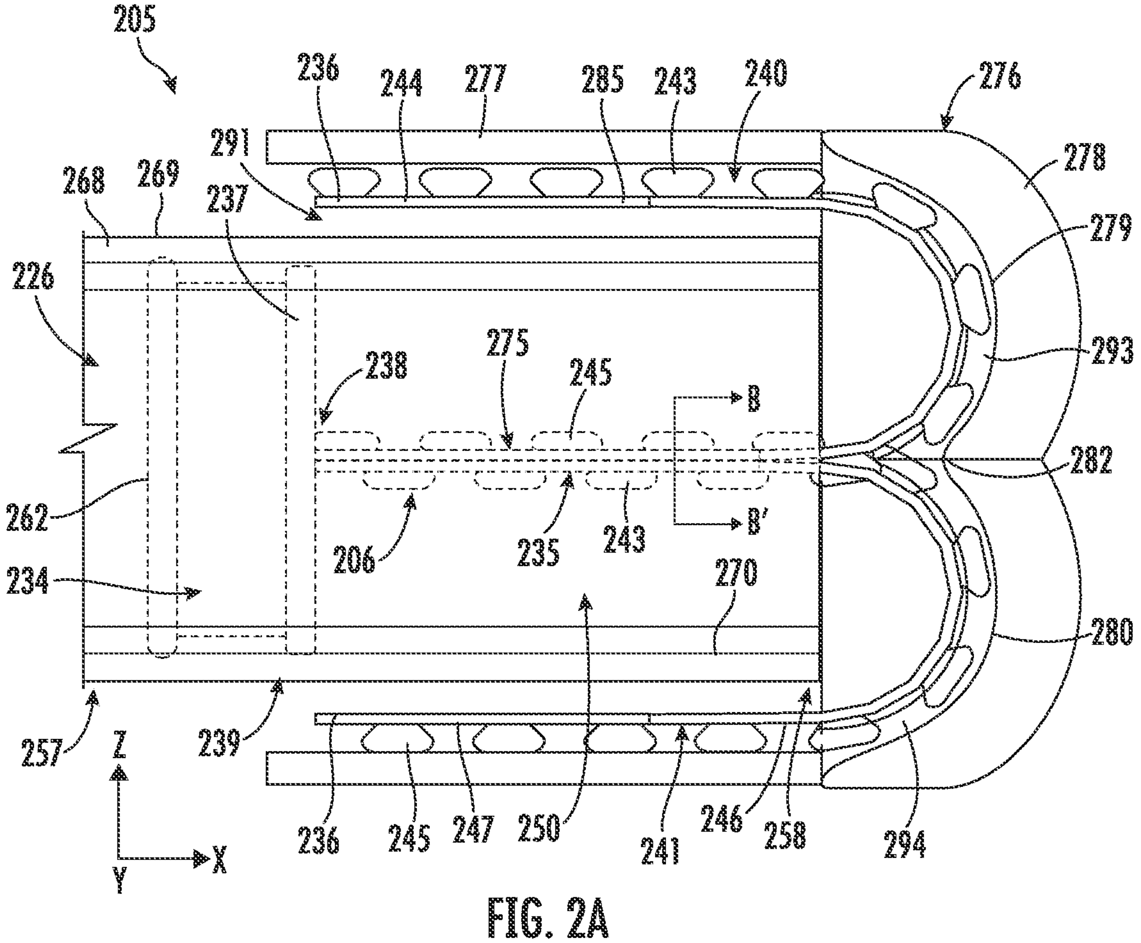
FIG. 2A illustrates a top view of a drive device of a delivery pump device, according to embodiments of the present disclosure.
Figure 2B:
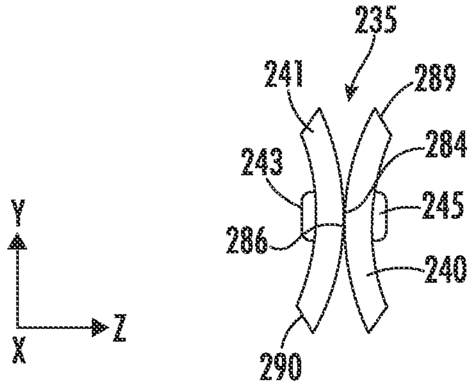
FIG. 2B illustrates a front view of a plunger shaft of the drive device of FIG. 2A, according to embodiments of the present disclosure.

As shown in FIG. 2B, the first and second components 240, 241 of the plunger shaft 235 may have a curved or bent profile. That is, the first component 240 may define a first crest 284 and the second component 241 may define a second crest 286, wherein the first and second crests 284, 286 extend towards, and become engaged with, one another. A top edge 289 and a bottom edge 290 of each of the first and second components 240, 241 may generally extend away from one another in opposite directions along the z-axis. Once joined together, the first and second components 240, 241 may resist bending in the +−z-directions as well in the +−y-directions. In various embodiments, the radius of curvature for the first and/or second components 240, 241 may be constant or varied. Furthermore, a first radius of curvature for the first component 240 may be different than a second radius of curvature for the second component 241. Although non-limiting, the curved first and second components 240, 241, may share some properties of a metal tape measure blade having a curved profile for the purpose of increasing tape rigidity and standout when the blade is in an extended position.

In some embodiments, the first component 240 may have a first bend resistance in a first direction (e.g., +z direction) and a second bend resistance in a second direction (e.g., −z direction). In the embodiment shown, the first bend resistance in the first direction is less than the second bend resistance in the second direction. Similarly, the second component 241 may have a first bend resistance in the first direction (e.g., +z direction) and a second bend resistance in the second direction (e.g., −z direction), wherein the first bend resistance in the first direction is greater than the second bend resistance in the second direction. As a result, the first and second components 240, 241 have a tendency to bend or coil away from one another unless engaged. Once engaged, the first and second components 240, 241 grip one another to form the rigid portion 275 within the reservoir 226.

When the reservoir 226 is empty or in a pre-filled state, as shown in FIG. 2A, the plunger head 234 is positioned at the first end 257 of the reservoir 226. In certain embodiments, the reservoir 226 may then be filled with fluid medicament, such as insulin, by opening an inlet port to the reservoir 226 and pumping in the insulin under sufficient hydraulic pressure. Thereafter, the inlet port may be closed. When the reservoir 226 is filled and the plunger head 234 has moved to or toward the second end 258 of the reservoir 226, the device 205 is ready to dispense the insulin. To begin doing so, the second end 236 of the first and second components 240, 241 may move towards the second end 258 of the reservoir 226, which causes engagement of the first and second components 240, 241, which in turn causes the first end 238 of the first and second components 240, 241 to push against the plunger head 234 and move the plunger head 234 towards the first end 257 of the reservoir 226.

The flexible plunger shaft 235 in the present embodiment may reduce the required length of the overall drive device 206 to approximately half, thus enabling the overall size of the drive device 206 to be reduced. More specifically, no leadscrew or tube nut are required in this drive device 206, which reduces part count and the overall length of the device 205. Such tube nuts typically extended along much of the length of the leadscrew, thereby increasing the required length of a clutch mechanism and overall drive system to approximately 2× the length of the leadscrew. In the advances disclosed herein, the tube nut and leadscrew are removed and the plunger shaft is modified to include one or more flexible components that fold or bend into a more compact configuration. As explained above, this reduces the required length of the drive device 206, overcoming the "2× length" problem, while also reducing the number of required parts for the device 205.

Figure 3A:
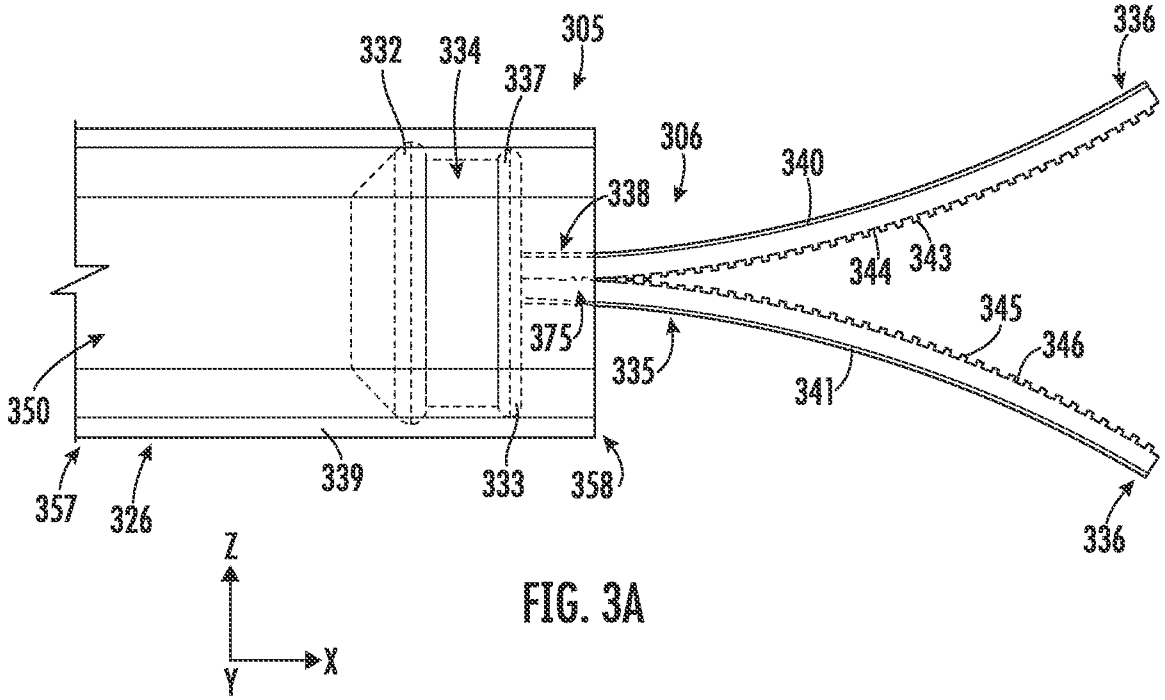
FIGS. 3A-3C illustrate various states of a drive device according to embodiments of the present disclosure.
Figure 3B:
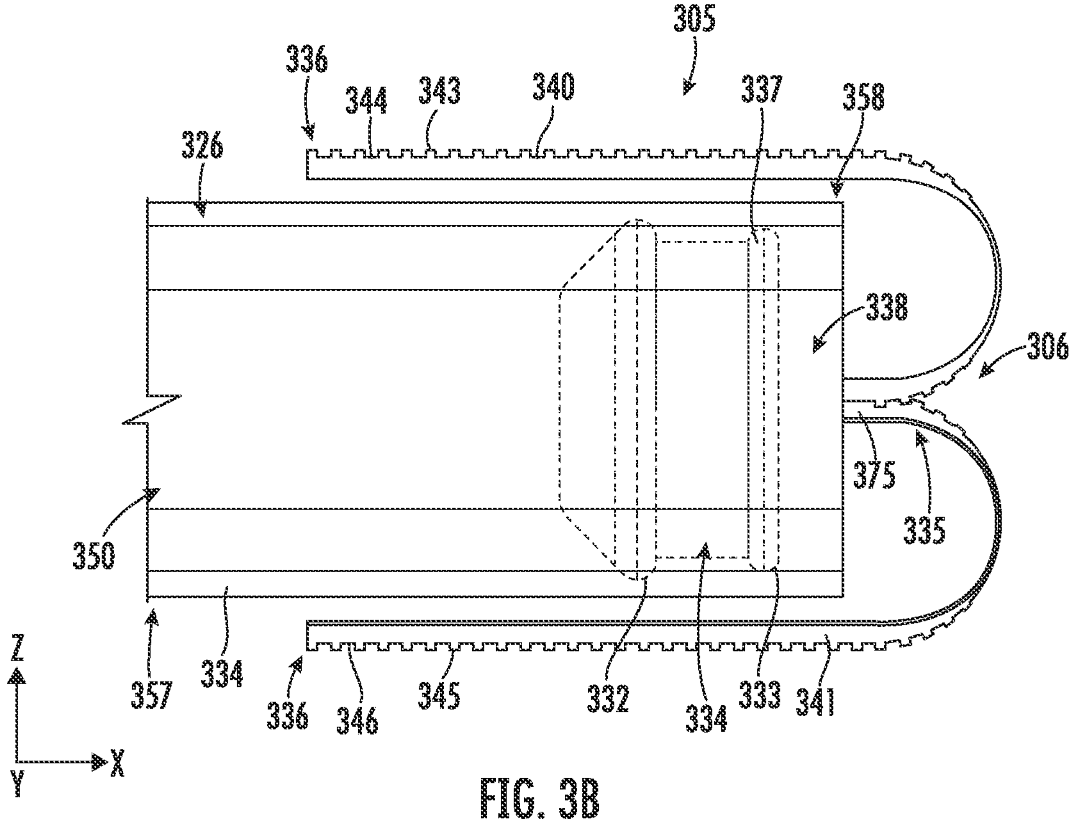
Figure 3C:
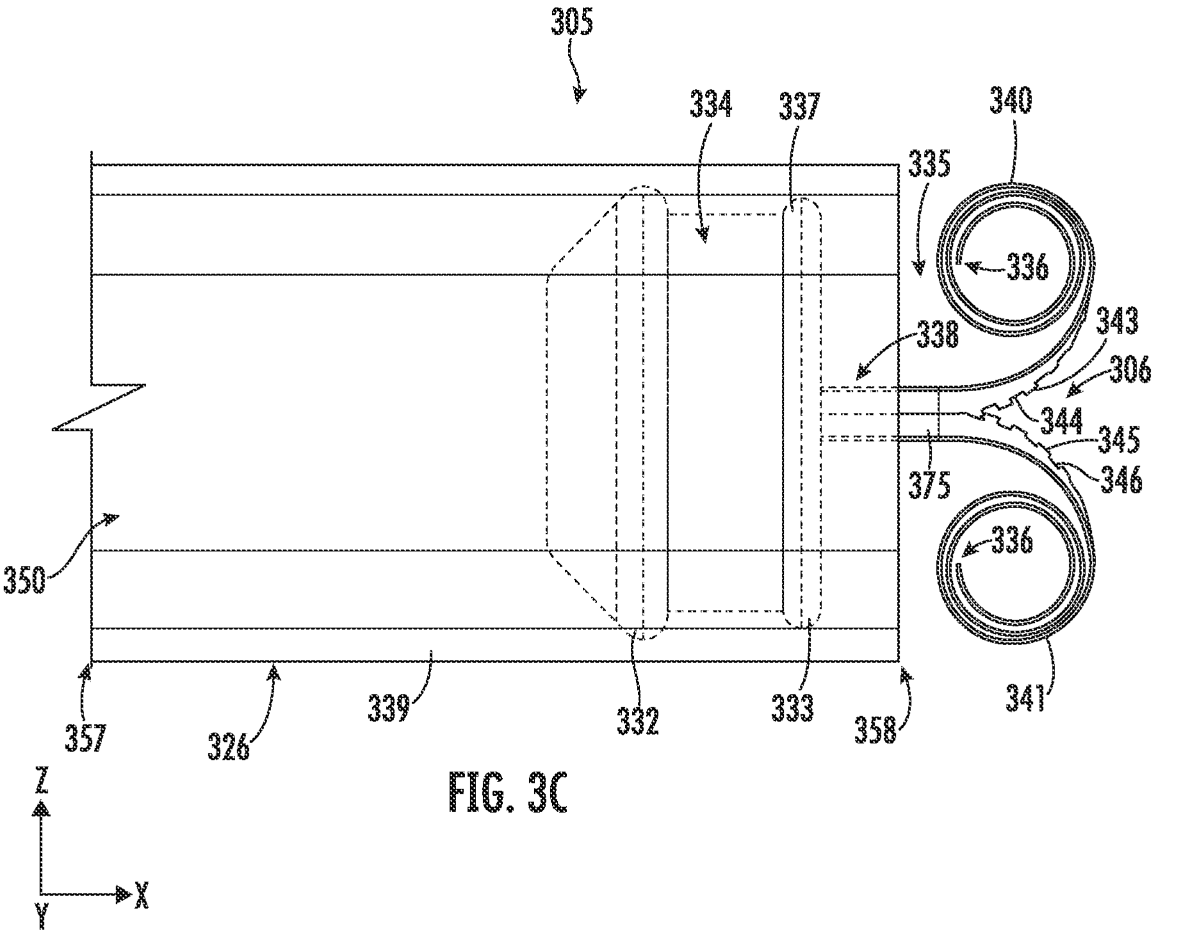

FIGS. 3A-3C demonstrate example drive devices 306 operating with a reservoir 326 of a device 305 according to embodiments of the present disclosure. As shown, each of the drive devices 306 may be positioned partially within an interior chamber 350 of a housing 339 of the reservoir 326. Although non-limiting, the housing 339 may be a circular or an oval-shaped cylinder including a first end 357 opposite a second end 358. The drive device 306 may include a plunger head 334 disposed within the interior chamber 350 of the housing 339. The plunger head 334 may include a sealing ring 332 (e.g., O-ring) extending around an outside perimeter thereof to create a liquid-tight seal between the plunger head 334 and the housing 339.

The drive device 306 may further include a plunger shaft 335 including a first component 340 coupleable with a second component 341 to bias the plunger head 334 between the first end 357 and the second end 358 of the reservoir 326. A first end 338 of the first and second components 340, 341 may be directly coupled to a plunger plate 337, which is secured to the plunger head 334. In some embodiments, the plunger plate 337 may include an outer sealing ring 333. In other embodiments, the first and second components 340, 341 may be directly coupled to the plunger head 334. Embodiments herein are not limited in this context. A second end 336 of the first and second components 340, 341 may extend outside of the housing 339.

As shown, the first component 340 may include a first plurality of alternating protrusions 343 and indentations 344. Similarly, the second component 341 may include a second plurality of alternating protrusions 345 and indentations 346. In some embodiments, indentations 344 and 346 may extend only partially through the first and second components 340, 341. In other embodiments, indentations 344 and 346 may be openings extending entirely through the first component 340 and the second component 341, respectively.

When the first and second components 340, 341 are brought together, protrusions 343 are operable to engage and interlock with indentations 346. Similarly, protrusions 345 are operable to engage and interlock with indentations 344. Coupling the first and second components 340, 341 together creates a rigid portion 375 of the plunger shaft 335, which helps drive the plunger head 334 towards the first end 357 of the reservoir 326. In those areas where the first and second components 340, 341 are not joined, the plunger shaft 335 may be relatively flexible. For example, as shown in FIG. 3B, the first and second components 340, 341 may wrap around the second end 358 of the reservoir 326 and extend substantially parallel to the exterior surface 369 of a wall 368. In other embodiments, as shown in FIG. 3C, the first and second components 340, 341 may curl up and coil in an area beyond the second end 358 of the housing 339. Although not shown, each of the first and second components 340, 341 may coil about a stationary support post. In other embodiments, each of the first and second components 340, 341 may coil about a gear-like rotating feature, which is operable to retract and advance the first and second components 340, 341.

Although not shown, the drive device 306 may further include a housing operable to contain, guide, and separate the first and second components 340, 341 of the plunger shaft 335, similar to the housing 276 shown in FIG. 2A. The housing in this embodiment may include a sidewall extending substantially parallel to the wall 368 of the reservoir 326, and an end wall connected to the sidewall. The sidewall of the housing and the wall 368 of the reservoir 326 may define a channel for containing and guiding the second end 336 of each of the first and second components 340, 341. In some embodiments, the end wall may include curved interior surfaces operable to bend the first and the second components 340, 340 around the second end 358 of the housing 339 as the first and second components 340, 341 move in and out of the reservoir 326. Each of the first and second components 340, 341 may be driven at the respective curves by a gear-like rotary drive (not shown). In other embodiments, the first and second components 340, 341 may be driven by a leadscrew or rack and pinion drive connected to the first and second components 340, 341. Embodiments herein are not limited in this context.

Similar to the housing 276 shown in FIG. 2A, the housing in this embodiment may include a crest or wedge operable to separate the first and second components 340, 341 from one another as the plunger head 334 moves towards the second end 358 of the reservoir 326. For example, as the reservoir 326 is filled with the liquid drug 125, the plunger head 334 and the rigid portion 375 of the plunger shaft 335 are forced towards the second end 358 of the reservoir 326. In some embodiments, the driving device, e.g., rotary drive and/or rack and pinion drive, may simulataneously pull the first and second components 340, 341 out of the reservoir 326. As the first and second components 340, 341 are forced against the wedge, the protrusions 343 become disengaged from the indentations 346 and the protrusions 345 become disengaged from the indentations 344. Decoupling the first and second components 340, 341 from one another eliminates, or at least shortens, the rigid portion 375 of the plunger shaft 335, and enables the first and second components 340, 341 to transition to a relatively flexible state in which each of the first and second components 340, 341 is bent or coiled into a more compact configuration.

Figure 3D:
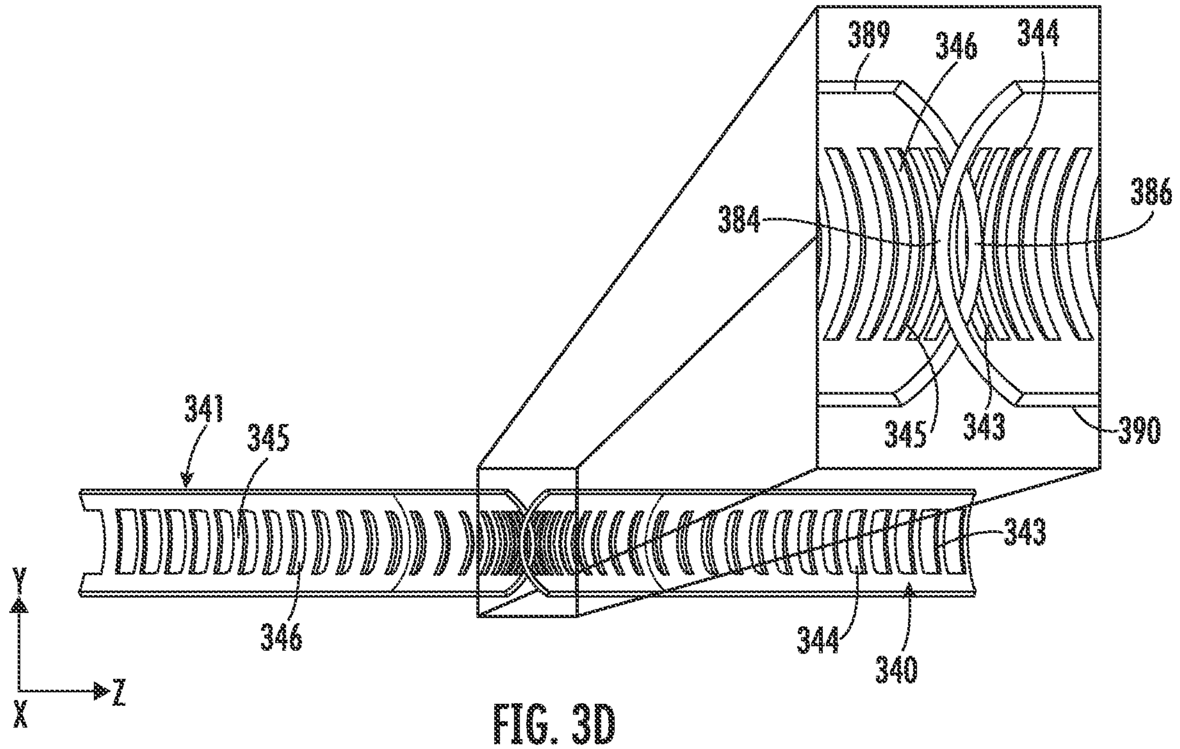
FIG. 3D illustrates a front view of a plunger shaft of the drive device of FIGS. 3A-3C, according to embodiments of the present disclosure.

As shown in FIG. 3D, the first and second components 340, 341 may have a curved or bent profile. That is, the first component 340 may define a first crest 384 and the second component 341 may define a second crest 386, wherein the first and second crests 384, 386 extend towards, and become engaged with, one another. More specifically, the protrusions 343 of the first component 340 at the first crest 384 may interlock with the indentations 346 of the second component 341 at the second crest 386. Similarly, the protrusions 345 of the second component 341 at the second crest 386 may interlock with the indentations 344 of the first component 340 at the first crest 384. A top edge 389 and a bottom edge 390 of each of the first and second components 340, 341 may generally extend away from one another in opposite directions along the z-axis. Once joined together, the first and second components 340, 341 may resist bending in the +−z-directions as well in the +−y-directions. In various embodiments, the radius of curvature for the first and/or second components 340, 341 may be constant or varied.

In some embodiments, the first component 340 may have a first bend resistance in a first direction (e.g., +z direction) and a second bend resistance in a second direction (e.g., −z direction). In the embodiment shown, the first bend resistance of the first component 340 in the first direction is less than the second bend resistance of the first component 340 in the second direction. Similarly, the second component 341 may have a first bend resistance in the first direction (e.g., +z direction) and a second bend resistance in the second direction (e.g., −z direction), wherein the first bend resistance of the second component 341 in the first direction is greater than the second bend resistance of the second component 341 in the second direction. As a result, the first and second components 340, 341 have a tendency to bend or coil away from one another unless engaged. Once engaged, the first and second components 340, 341 transition from a stressed, coiled state to an unstressed rigid state to form the rigid portion 375 within the reservoir 326.

FIGS. 4A-4D demonstrate an example drive device 406 operating with a reservoir (not shown) of a device 405 according to embodiments of the present disclosure. The drive device 406 may include a housing 407 coupleable with the reservoir. In some embodiments, the housing 407 may include an attachment ring 408, which may be secured to the second end of the reservoir. The housing 407 may further include a support beam 409 extending from the attachment ring 408. Although non-limiting, the housing attachment ring 408 may be a circular or an oval-shaped cylinder selected to compliment the shape of the reservoir. In other embodiments, the shape of the attachment ring 408 and/or the housing 407 may be different than the housing of the reservoir.

As shown, the support beam 409 may include a first plate 410 connected to a second plate 411 by a cross member 412. Although non-limiting, the first plate 410, the second plate 411, and the cross member 412 may be arranged similar to an I-beam. The first and second plates 410, 411 may include one or more openings 413 for receiving shafts 414 of respective first and second drive wheels 415, 416. In some embodiments, the first and second drive wheels 415, 416 may be pinion gears each having a plurality of teeth 417 operable to engage respective first and second components 440, 441 of a plunger shaft 435. More specifically, the teeth 417 may extend through a plurality of openings 444 of the first component 440 and a plurality of openings 446 of the second component 441. In some embodiments, a first end 438 of the first and second components 440, 441 may be directly coupled to a plunger plate or to a plunger head within the reservoir. A second end 436 of the first and second components 440, 441 may extend outside of the reservoir.

As shown, the first component 440 may include a first plurality protrusions 443 alternating with the openings 444. Similarly, the second component 441 may include a second plurality protrusions 445 alternating with the openings 446. In some embodiments, the first plurality of protrusions 443 and the second plurality of protrusions 445 may be curved members extending vertically (e.g., in the y-direction) between a top edge 489 and a bottom edge 490 of respective first and second components 440, 441.

When the first and second components 440, 441 are brought together, the first plurality of protrusions 443 of the first component 440 are operable to engage and interlock with the openings 446 of the second component 441. Similarly, the second plurality of protrusions 445 of the second component 441 are operable to engage and interlock with the openings 444 of the first component 440. Coupling the first and second components 440, 441 together creates a rigid portion 475 of the plunger shaft 435, which helps drive the plunger head towards the first end of the reservoir to expel a liquid (e.g., insulin) therefrom. Prior to being joined, each of the first and second components 440, 441 may be relatively flexible such that each of the first and second components 440, 441 may wrap/coil around the first and second drive wheels 415, 416 and extend along an opposite exterior of the housing 407.

Figure 4A:
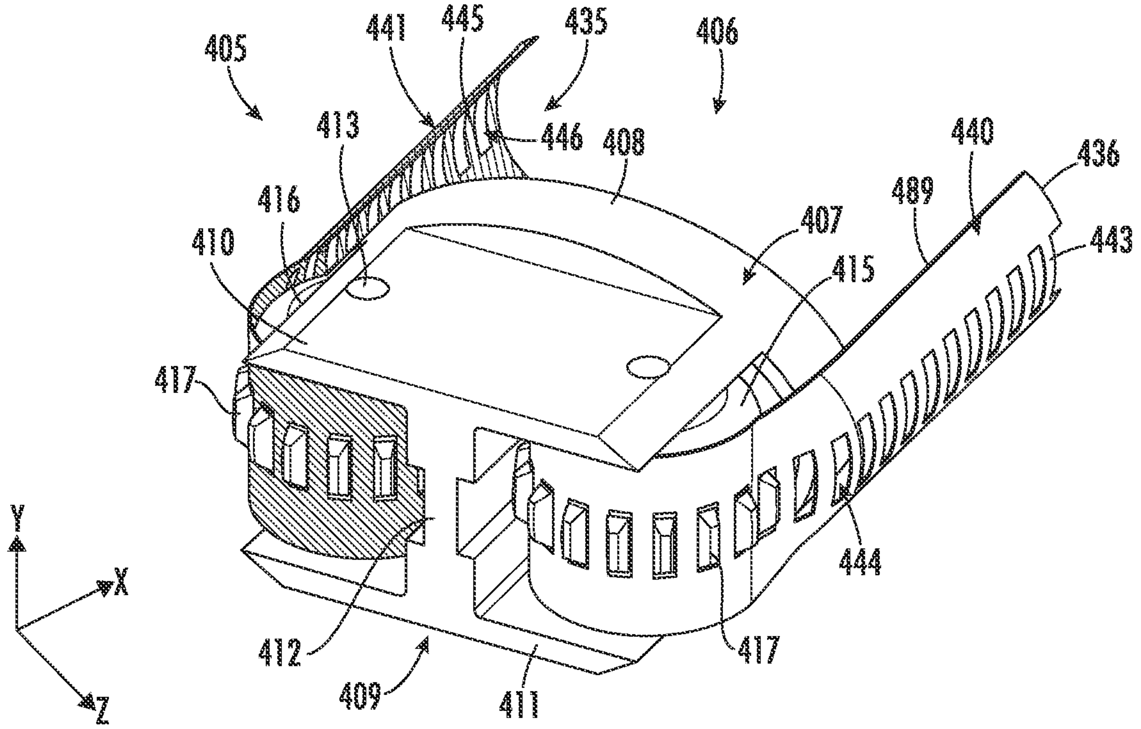
FIG. 4A illustrates a perspective view of a drive device of a delivery pump device, according to embodiments of the present disclosure.
Figure 4B:
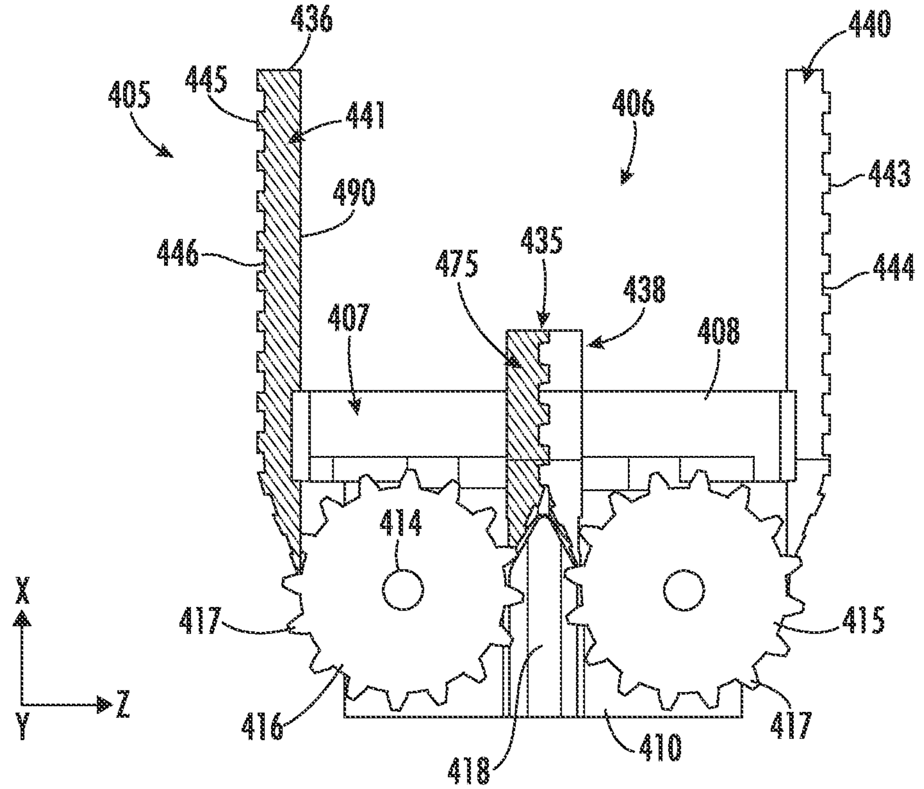
FIG. 4B illustrates a top view of the drive device of FIG. 4A, according to embodiments of the present disclosure.
Figure 4C:
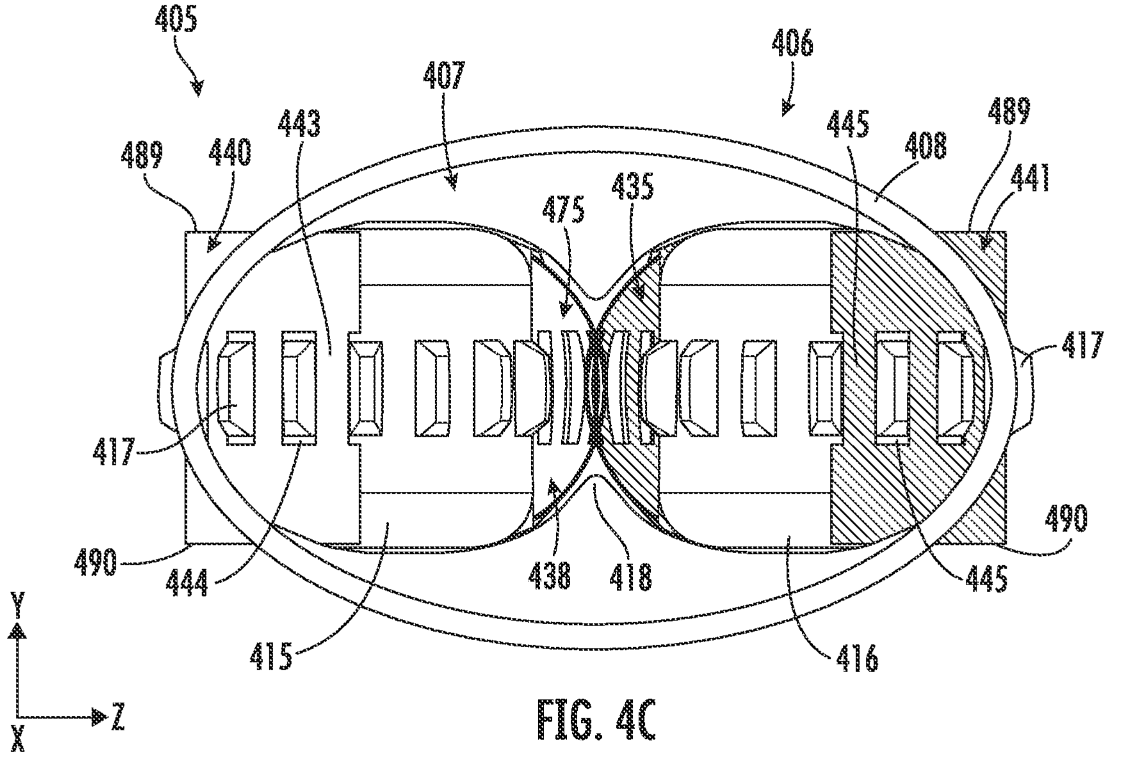
FIG. 4C illustrates a front view of the drive device of FIG. 4A, according to embodiments of the present disclosure.
Figure 4D:
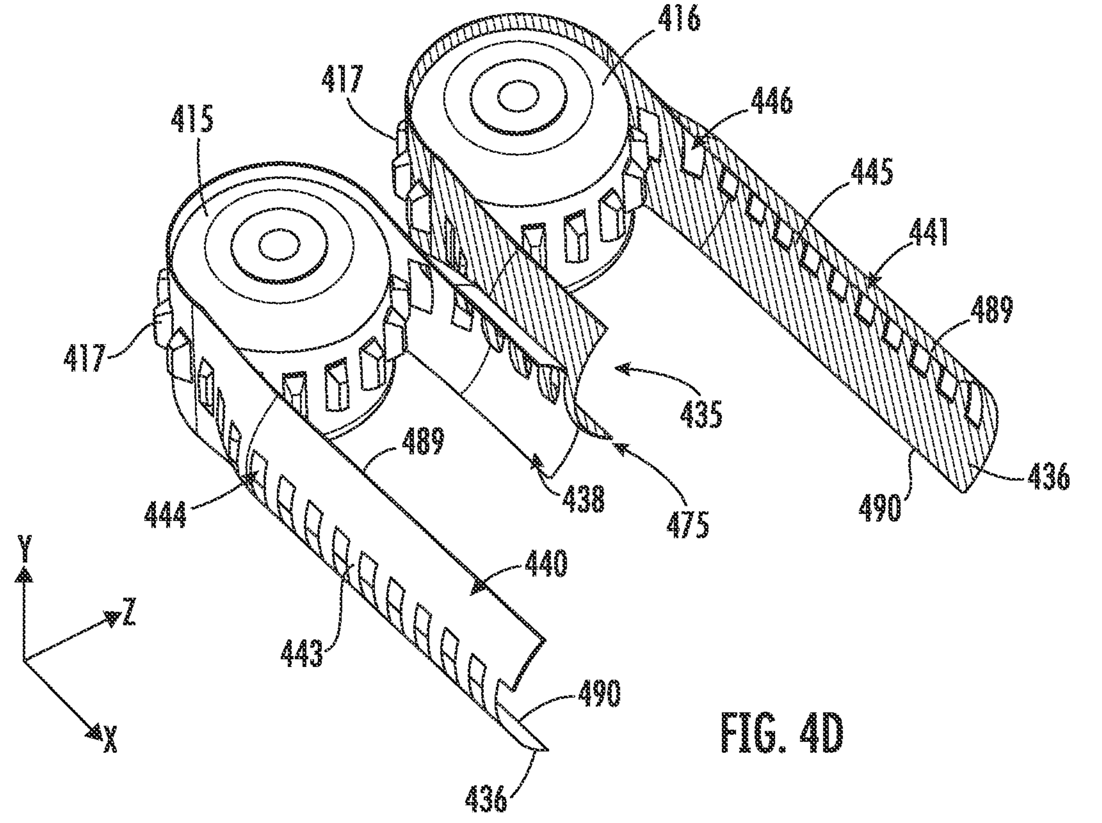
FIG. 4D illustrates a perspective view of the drive device of FIG. 4A, according to embodiments of the present disclosure.

As best shown in FIG. 4B and FIG. 4C, the housing 407 may include one or more crests or wedges 418 operable to separate the first and second components 440, 441 from one another as the plunger head moves towards the housing 407. For example, as the reservoir is filled with the liquid drug 125, the plunger head and the rigid portion 475 of the plunger shaft 435 are forced towards the second end of the reservoir by the first and second drive wheels 415, 416. As the first and second components 440, 441 are forced against the wedge(s) 418, the first protrusions 443 become disengaged from the openings 446 and the second protrusions 445 become disengaged from the openings 444. Decoupling the first and second components 440, 441 from one another eliminates, or shortens, the rigid portion 475 of the plunger shaft 435, and enables the first and second components 440, 441 to transition to a relatively flexible state, which allows each of the first and second components 440, 441 to bend or coil into a more compact configuration.

As further shown, the first and second components 440, 441 may have a curved or bent profile. That is, the first component 440 may define a first crest 484 (or a series of first crests along each protrusion 443) and the second component 441 may define a second crest 486 (or series of second crests along each protrusion 445), wherein the first and second crests 484, 486 extend towards, and become engaged with, one another. The top edge 489 and the bottom edge 490 of each of the first and second components 440, 441 may generally extend away from one another in opposite directions along the z-axis. Once joined together, the rigid portion 475 of the first and second components 440,

441 may resist bending in the +−z-direction as well in the +−y-direction. In various embodiments, the radius of curvature for the first and/or second components 440, 441 may be constant or varied.

In some embodiments, the first component 440 may have a first bend resistance in a first direction (e.g., +z direction) and a second bend resistance in a second direction (e.g., −z direction). In the embodiment shown, the first bend resistance in the first direction is less than the second bend resistance in the second direction. Similarly, the second component 441 may have a first bend resistance in the first direction (e.g., +z direction) and a second bend resistance in the second direction (e.g., −z direction), wherein the first bend resistance in the first direction is greater than the second bend resistance in the second direction. As a result, the first and second components 440, 441 have a tendency to bend or coil away from one another unless engaged. Once engaged, the first and second components 440, 441 transition from a stressed, coiled state to an unstressed rigid state to form the rigid portion 475 within the reservoir 426.

Figure 5A:
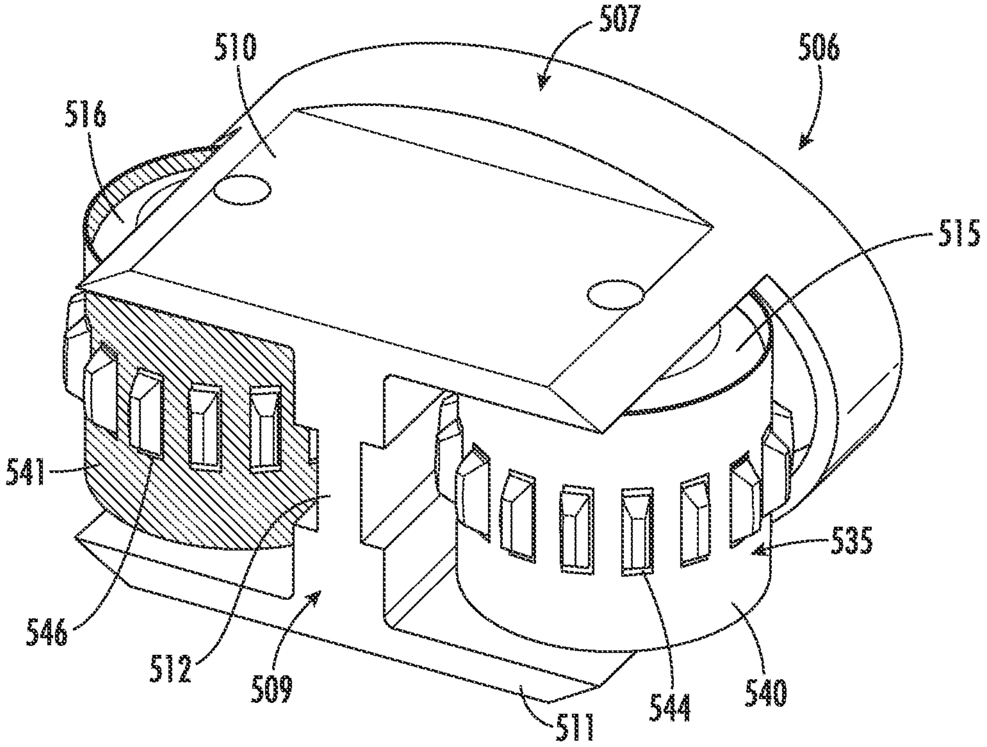
FIGS. 5A-5B illustrate perspective views of a drive device of a delivery pump device, according to embodiments of the present disclosure.
Figure 5B:
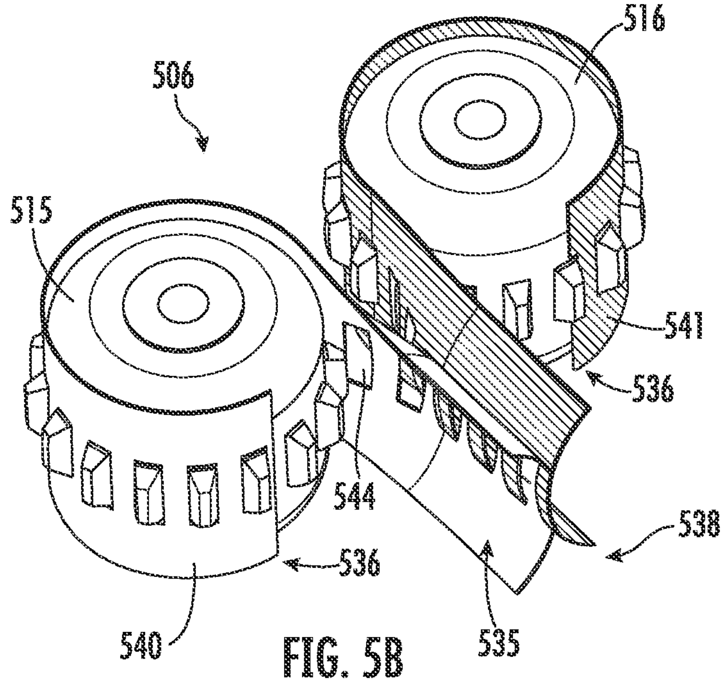

FIGS. 5A-5B demonstrate an example drive device 506 operating with a reservoir (not shown) of a device according to embodiments of the present disclosure. The drive device 506 is similar in many aspects to the drive device 406 described above. As such, only certain aspects of the drive device 506 will hereinafter be described for the sake of brevity. The drive device 506 may include a housing 507 coupleable with the reservoir, wherein the housing 507 may include a support beam 509 extending from an attachment ring 508. As shown, the support beam 509 may include a first plate 510 connected to a second plate 511 by a cross member 512.

The drive device 506 may include first and second drive wheels 515, 516. The first and second drive wheels 515, 516 may be pinion gears each having a plurality of teeth 517 operable to engage respective first and second components 540, 541 of a plunger shaft 535. More specifically, the teeth 517 may extend through a plurality of openings 544 of the first component 540 and a plurality of openings 546 of the second component 541. In some embodiments, a first end 538 of the first and second components 540, 541 may be directly coupled to a plunger plate or to a plunger head within the reservoir. A second end 536 of the first and second components 540, 541 may wrap around the first drive wheel 515 and the second drive wheel 516, respectively. In this embodiment, the first and second drive wheels 515, 516 may have a circumference greater than a maximum required plunger travel distance, which allows the first and second components 540, 541 to coil around the first and second drive wheels 515, 516 instead of, e.g., traveling along an exterior of the housing 507 and/or the reservoir. This embodiment may eliminate the need for additional housing channels for the first and second components 540, 541 of plunger shaft 535, while still allowing for easier assembly and size savings for the drive device 506.

Figure 6A:
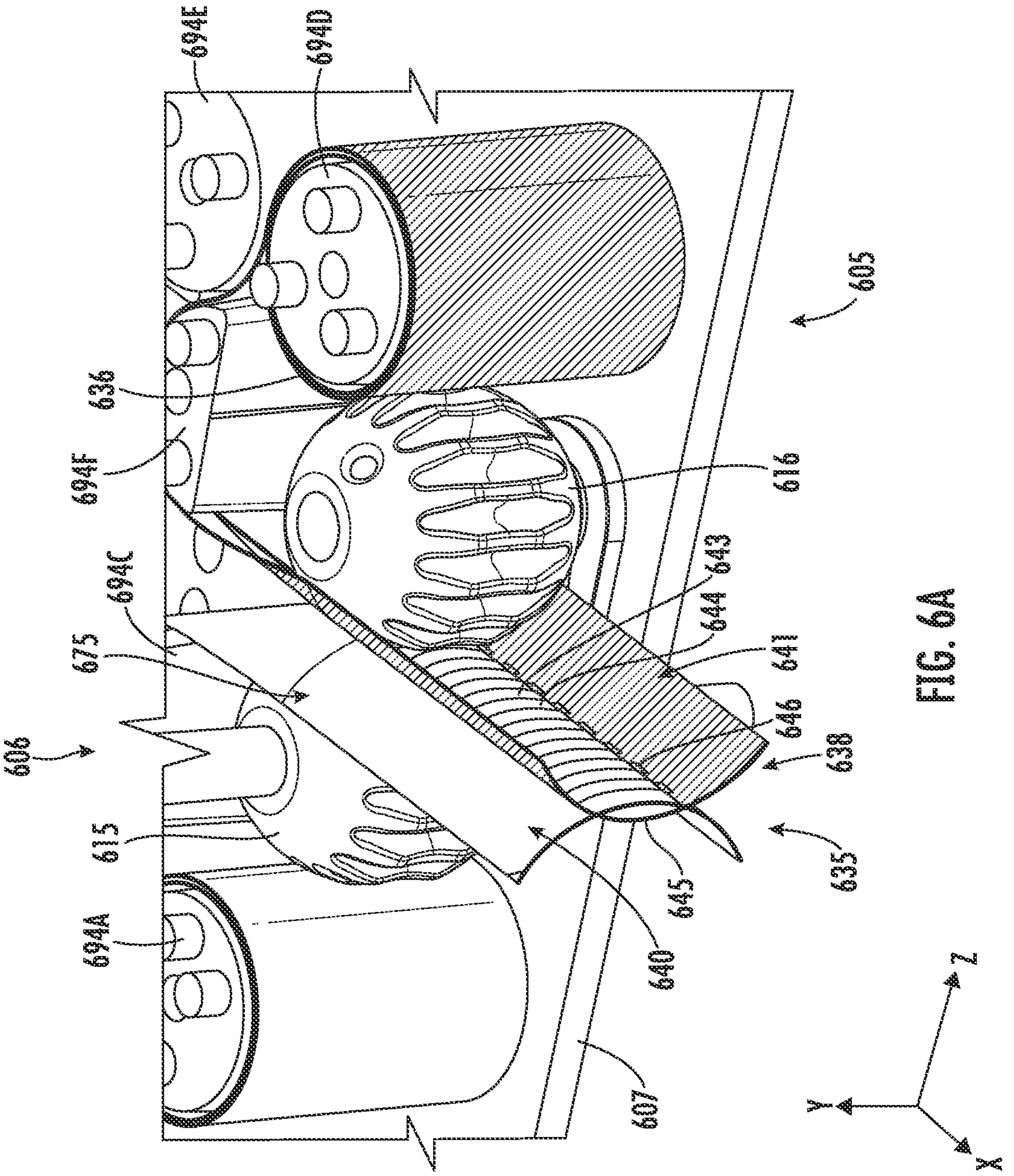
FIG. 6A illustrates a perspective view of a drive device of a delivery pump device, according to embodiments of the present disclosure.
Figure 6B:
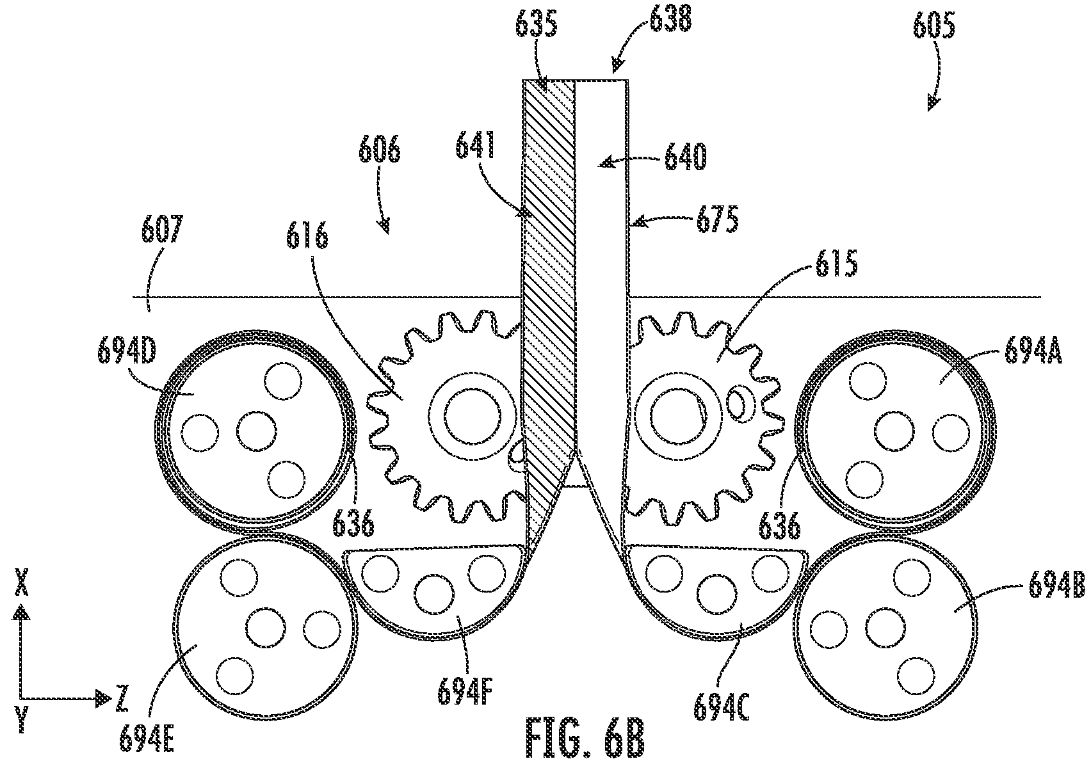
FIG. 6B illustrates a top view of the drive device of FIG. 6A, according to embodiments of the present disclosure.
Figure 6C:
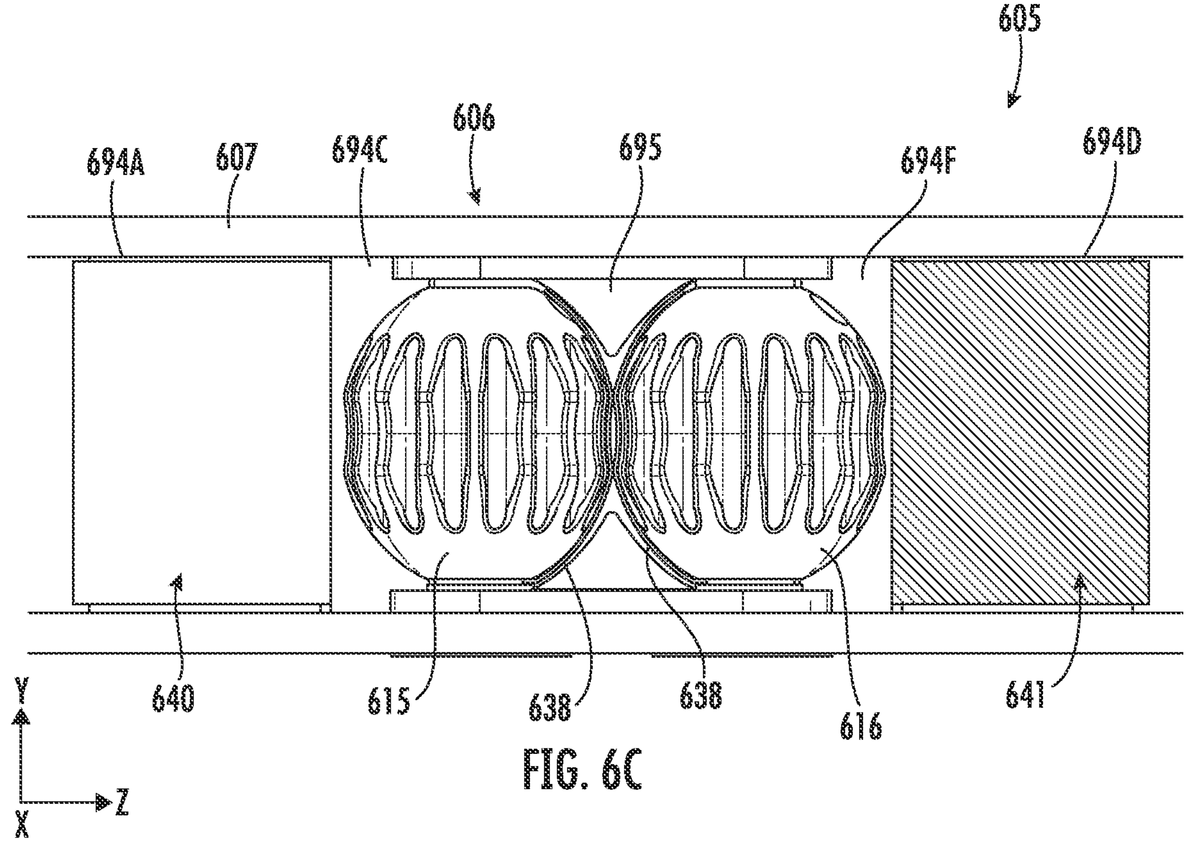
FIG. 6C illustrates a front view of the drive device of FIG. 6A, according to embodiments of the present disclosure.

FIGS. 6A-6C demonstrates an example drive device 606 operating with a reservoir (not shown) of a device 605 according to embodiments of the present disclosure. The drive device 606 may include a plunger shaft 635 including a first component 640 coupleable with a second component 641 to bias a plunger head (not shown) within the reservoir. A first end 638 of the first and second components 640, 641 may be coupled to the plunger head, while a second end 636 of the first and second components 640, 641 may wrap around one or more support posts 694A-694F, as will be described in greater detail herein. The drive device 606 may include a housing 607 coupleable with the reservoir.

The first component 640 may include a first plurality of alternating protrusions 643 and indentations 644. Similarly, the second component 641 may include a second plurality of alternating protrusions 645 and indentations 646. In some embodiments, indentations 644 and 646 may be openings extending entirely through the first component 640 and the second component 641, respectively. In other embodiments, indentations 644 and 646 may extend only partially through the first and second components 640, 641.

The first and second components 640, 641 may have a curved or bent profile. That is, the first and second components 640, 641 may define crests facing and extending towards one another. A top edge 689 and a bottom edge 690 of each of the first and second components 640, 641 may generally extend away from one another in opposite directions along the z-axis. Once joined together, the first and second components 640, 641 may resist bending in the +−z-directions as well in the +−y-directions. In various embodiments, the radius of curvature for the first and/or second components 640, 641 may be constant or varied.

In some embodiments, the first component 640 may have a first bend resistance in a first direction (e.g., +z direction) and a second bend resistance in a second direction (e.g., −z direction). In the embodiment shown, the first bend resistance in the first direction is less than the second bend resistance in the second direction. Similarly, the second component 641 may have a first bend resistance in the first direction (e.g., +z direction) and a second bend resistance in the second direction (e.g., −z direction), wherein the first bend resistance in the first direction is greater than the second bend resistance in the second direction. As a result, the first and second components 640, 641 have a tendency to bend or coil away from one another unless engaged. Once engaged, the first and second components 640, 641 transition from a stressed, coiled state to an unstressed rigid state to form a rigid portion 675 within the reservoir.

When the first and second components 640, 641 are brought together, protrusions 643 engage and interlock with indentations 646. Similarly, protrusions 645 engage and interlock with indentations 644. Coupling the first and second components 640, 641 together creates the rigid portion 675 of the plunger shaft 635, which helps drive the plunger head within the reservoir.

The drive device 606 may include first and second drive wheels 615, 616 coupled to the housing 607. The first and second drive wheels 615, 616 may be pinion gears each having a plurality of teeth 617 operable to engage respective first and second components 640, 641 of the plunger shaft 635. More specifically, the teeth 617 may extend through the indentations 644 of the first component 640 and through the indentations 646 of the second component 641. Placing the first and second drive wheels 615, 616 after the merging of the first and second components 640, 641 creates a solid beam of the rigid portion 675 between the drive and the plunger to further reduce the risk of buckling. In some embodiments, a secondary coiling or direction changing bearing/bushing (not shown) may be present downstream of the first and second drive wheels 615, 616. To further ensure drive engagement, a set of curvature guides 695 (FIG. 6C) may be included to allow the first and second components 640, 641 to maintain a curved shape as the plunger 635 is driven by the first and second drive wheels 615, 616. Although not shown, the first and second drive wheels 615, 616 may be mated with each other using one or more additional gears for each drive wheel to ensure the first and second drive wheels 615, 616 are both driving the plunger shaft 635 together.

As best shown in FIG. 6B, the drive device 606 may include the plurality of support posts 694A-694F located external to the reservoir. The support posts 694A-694F may be arranged adjacent the first and second drive wheels 615, 616 for guiding the first and second components 640, 641 as the plunger shaft 635 is advanced and retracted. In some embodiments, the first component 640 may wrap around support post 694A and pass between support posts 694B, 694C before reaching the first and second drive wheels 615, 616. Similarly, the second component 641 may wrap around support post 694D and pass between support posts 694E, 694F. The plurality of support posts 694A-694F may be positioned close together to minimize an overall size of the drive device 606. As shown, support posts 694C, 694F may have a half-cylinder shape to allow the support posts 694C, 694F to be positioned closer to the first drive wheel 615 and to the second drive wheel 616, respectively. In other embodiments, support posts 694B, 694E may also have a half-cylinder shape. Other shapes, configurations, and/or number of support posts may be possible in alternative embodiments. Furthermore, in some embodiments, the second ends 636 of the first and second components 640, 641 may wrap around and extend along an exterior of the reservoir instead of terminating along support post 694A and support post 694D, respectively.

Figure 7A:
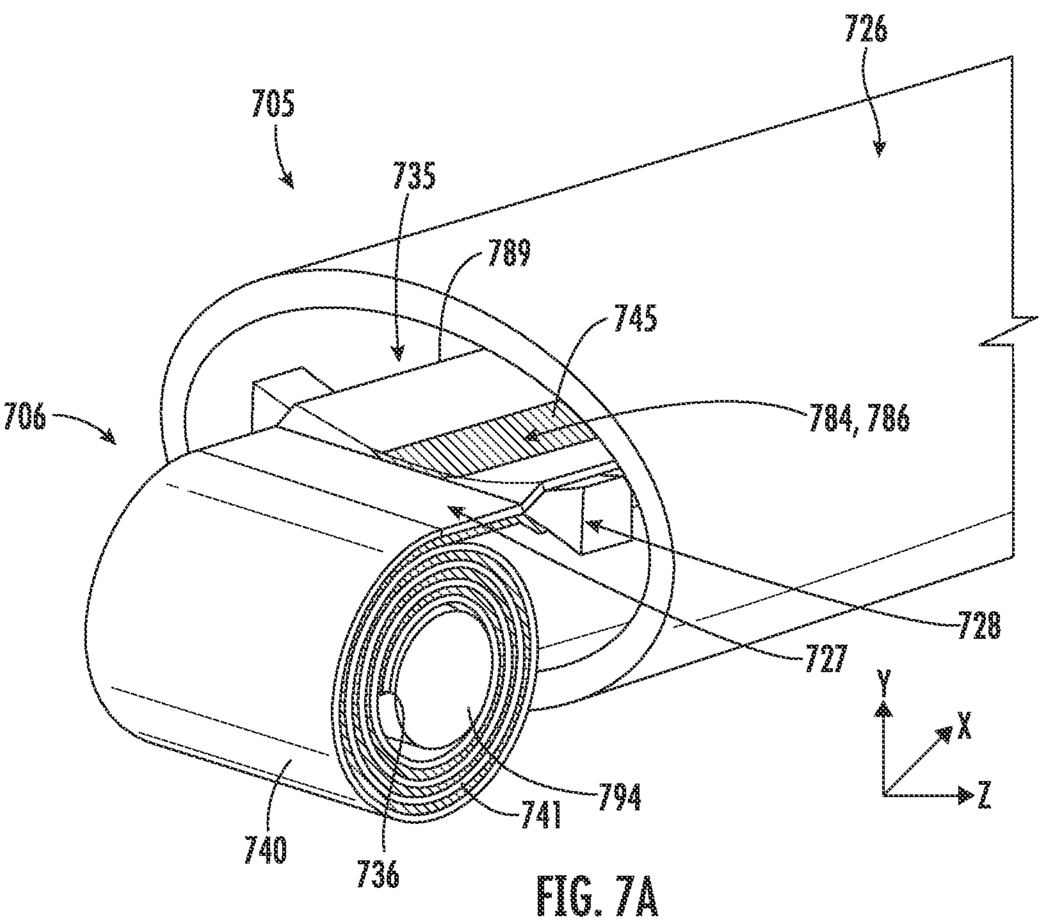
FIG. 7A illustrates a perspective view of a drive device of a delivery pump device, according to embodiments of the present disclosure.
Figure 7B:
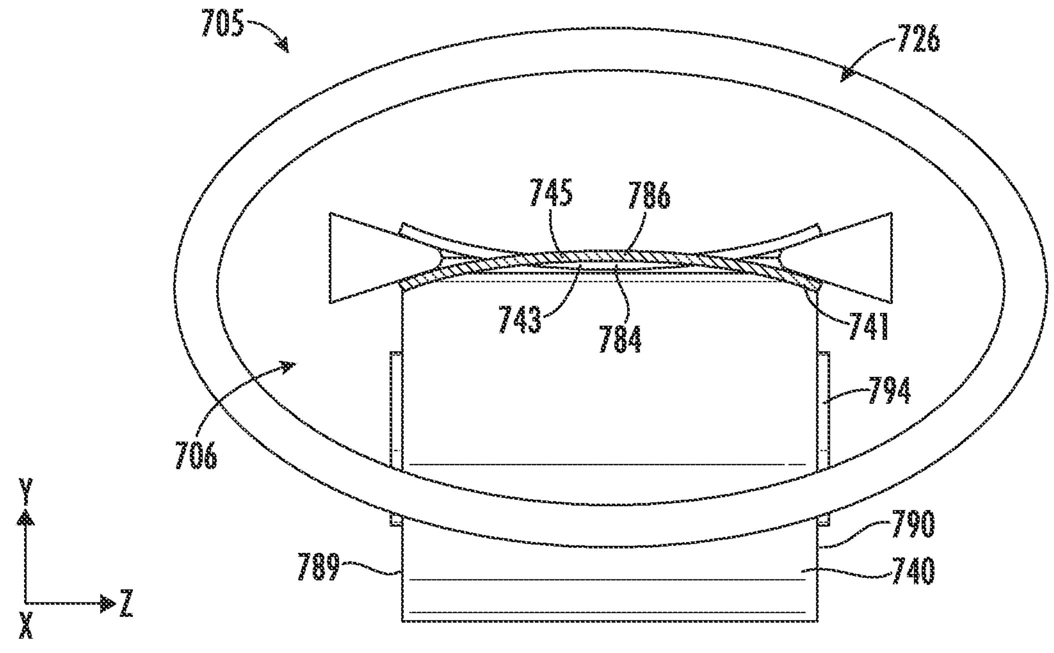
FIG. 7B illustrates a front view of the drive device of FIG. 7A, according to embodiments of the present disclosure.

FIGS. 7A-7B demonstrate an example drive device 706 operating with a reservoir 726 of a device 705 according to embodiments of the present disclosure. The drive device 706 may include a plunger shaft 735 including a first component 740 coupleable with a second component 741 to bias a plunger head (not shown) within the reservoir 726. A first end (not visible) of the first and second components 740, 741 may be coupled to the plunger head, while a second end 736 of the first and second components 740, 741 may coil or wrap around a support post 794, which may be an axle. Although not shown, the drive device 706 may include a housing coupleable with the reservoir 726.

The first component 740 may include a first plurality of protrusions 743 extending outwardly from a first strip of material, and a first plurality of indentations (not shown) extending into the first strip of material. Similarly, the second component 741 may include a second plurality of protrusions 745 extending outwardly from a second strip of material, and a second plurality of indentations (not shown) extending into the second strip of material. In some embodiments, the first and second plurality of indentations may be openings extending entirely through the first strip of material and the second strip of material, respectively. In other embodiments, the first and second plurality of indentations extend only partially through the first strip of material and the second strip of material, respectively.

When the plunger shaft 735 is dispensed from the support post 794, the first and second components 740, 741 are initially adjacent and parallel to one another in a transition area 727. In some embodiments, a gear or pinion (not shown) can be driven at the transition area 727 to provide a uniform distance for the first and second components 740, 741 to travel while also offering equal pulse sizes. As the plunger shaft 735 continues to advance, the first and second components 740, 741 are separated from one another by a separator 728. Although non-limiting, the separator 728 may be a pair of wedges positioned against a first edge 789 and a second edge 790 of each of the first and second components 740, 741. As the first and second components 740, 741 pass the separator 728, the first and second components 740, 741 transition from a stressed, coiled state to an unstressed rigid state to form a rigid portion 775 within the reservoir 726. In the unstressed state, the first and second components 740, 741 may have a curved or bent profile. That is, the first component 740 may define a first crest 784 (or series of crests) and the second component 741 may define and a second crest 786 (or series of crests), wherein the first and second crests 784, 786 extend towards and interlock with one another. More specifically, as the first and second components 740, 741 are brought together, protrusions 743 of the first component 740 are operable to engage and interlock with the indentations of the second component 741 and the protrusions 745 of the second component 741 are operable to engage and interlock with the indentations of the first component 740. With the first and second components 740, 741 meshed together and in a rigid state, the first and second components 740, 741 resist bending in the +−z-directions as well in the +−y-directions as the plunger shaft 735 drives the plunger head within the reservoir 726.

In some embodiments, the first and second components 740 can be contained in a shell or container surrounding the support post 794 to prevent the first and second components 740, 741 from expanding an undesirable amount. The shell or container may be contained within a chassis of the housing, allowing the first and second components 740, 741 to coil up smoothly during a variable fill of the reservoir 726.

Figure 8A:
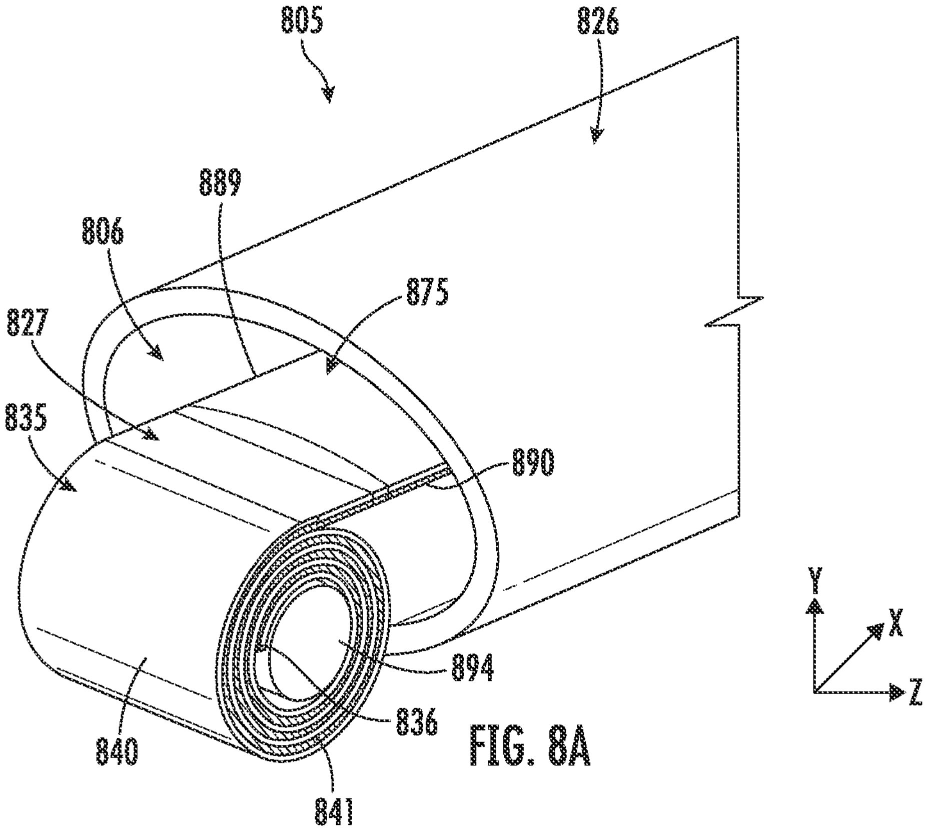
FIG. 8A illustrates a perspective view of a drive device of a delivery pump device, according to embodiments of the present disclosure.
Figure 8B:
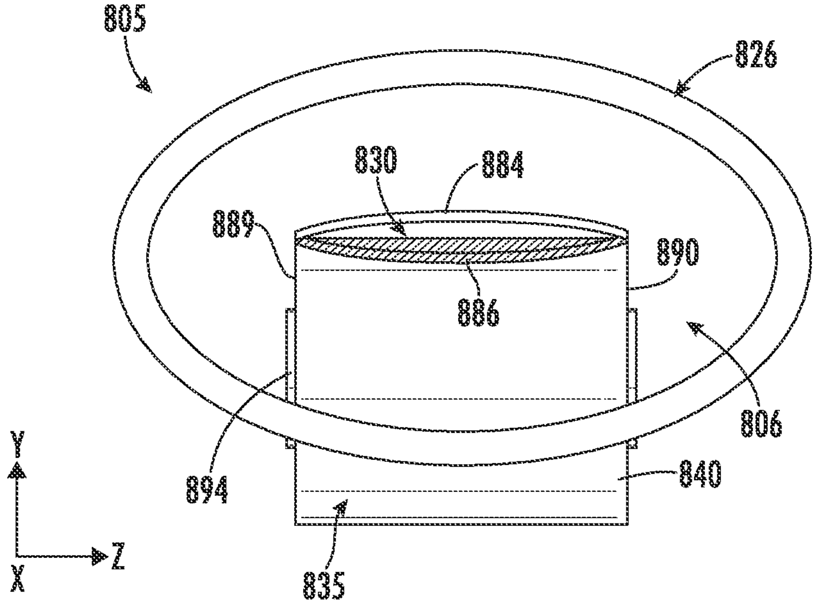
FIG. 8B illustrates a front view of the drive device of FIG. 8A, according to embodiments of the present disclosure.

FIGS. 8A-8B demonstrate an example drive device 806 operating with a reservoir 826 of a device 805 according to embodiments of the present disclosure. The drive device 806 is similar in many aspects to the drive device 706 described above. As such, only certain aspects of the drive device 806 will hereinafter be described for the sake of brevity. The drive device 806 may include a plunger shaft 835 including a first component 840 coupled with a second component 841 to bias a plunger head (not shown) within the reservoir 826. A second end 836 of the first and second components 840, 841 may be coiled about a support post 894. In this embodiment, the first and second components 840, 841 may be joined (e.g., welded, fastened, connected by adhesive) at respective first and second edges 889, 890. By fusing the first and second edges 889, 890 the first and second components 840, 841 may maintain relative positioning during dispensing.

When the plunger shaft 835 is dispensed from support post 894, the first and second components 840, 841 are initially parallel and flat in a transition area 827. In some embodiments, the plunger shaft 835 can be driven by a gear or pinion at the transition area 827. Although not shown, one or both of the first and second components 840, 841 may include a plurality of openings for engaging a set of teeth of the gear/pinion. As the plunger shaft 835 continues to advance, the first and second components 840, 841 are partially separated from one another to form a gap 830 therebetween. More specifically, the first and second components 840, 841 transition from a stressed, coiled state to an unstressed rigid state to form a rigid portion 875 of the plunger shaft 835 within the reservoir 826. In the unstressed state, the first and second components 840, 841 may have a curved or bent profile with the gap 830 formed therebetween. That is, the first component 840 may define a first crest 884 and the second component 841 may define and a second crest 886, wherein the first and second crests 884, 886 point or extend away from one another. With the first and second components 840, 841 joined together and in a rigid state, with a curved or bent profile and gap 830 formed therebetween, the first and second components 840, 841 resist bending within the reservoir 826.

Figure 9:
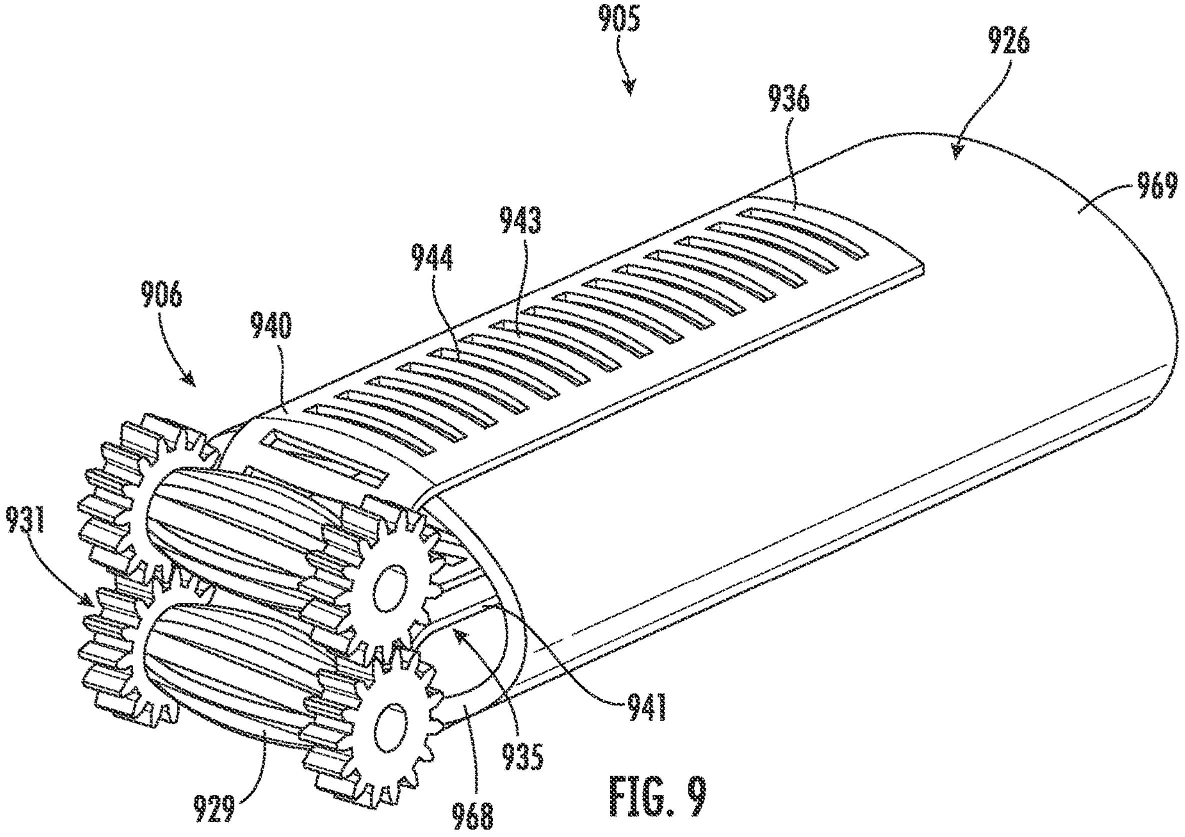
FIG. 9 illustrates a perspective view of a drive device of a delivery pump device, according to embodiments of the present disclosure.

FIG. 9 demonstrates an example drive device 906 operating with a reservoir 926 of a device 905 according to embodiments of the present disclosure. The drive device 906 is similar in many aspects to the drive device 706 described above. As such, only certain aspects of the drive device 906 will hereinafter be described for the sake of brevity. The drive device 906 may include a plunger shaft 935 including a first component 940 coupled with a second component 941 to bias a plunger head (not shown) within the reservoir 926. A second end 936 of the first and second components 940, 941 may extend along an exterior surface 969 of the reservoir 926.

The first component 940 may include a first plurality of alternating protrusions 943 and openings 944. Similarly, the second component 941 may include a second plurality of alternating protrusions and openings (not shown). Each of the openings may receive corresponding teeth 929 of a pair of drive devices 931 (e.g., pinion gears) for engaging and biasing the first and second components 940, 941.

As the first and second components 940, 941 are meshed together, the first and second components 940, 941 transition from a stressed, coiled state to an unstressed rigid state to form a rigid portion within the reservoir 926. In the unstressed state, the first and second components 940, 941 may have a curved or bent profile. That is, the first and second components 940, 941 may define respective crests, which extend towards and interlock with one another. More specifically, protrusions 943 of the first component 940 are operable to engage and interlock with the openings of the second component 941 and the protrusions of the second component 941 are operable to engage and interlock with the openings 944 of the first component 940. With the first and second components 940, 941 meshed together and in a rigid state, the plunger shaft 935 resists bending as it drives the plunger head within the reservoir 726.

Although not shown, the drive device 906 may further include a housing operable to contain, guide, and separate the first and second components 940, 941 of the plunger shaft 935. Similar to the housing 276 shown in FIG. 2A, the housing in this embodiment may include a sidewall extending substantially parallel to a wall 968 of the reservoir 926, and an end wall connected to the sidewall. The sidewall of the housing and the wall 968 of the reservoir 926 may define a channel for containing and guiding the second end 936 of each of the first and second components 940, 941. In some embodiments, the end wall may include curved interior surfaces operable to bend and guide the first and the second components 940, 940 around the reservoir 926. Embodiments herein are not limited in this context.

Figure 10:
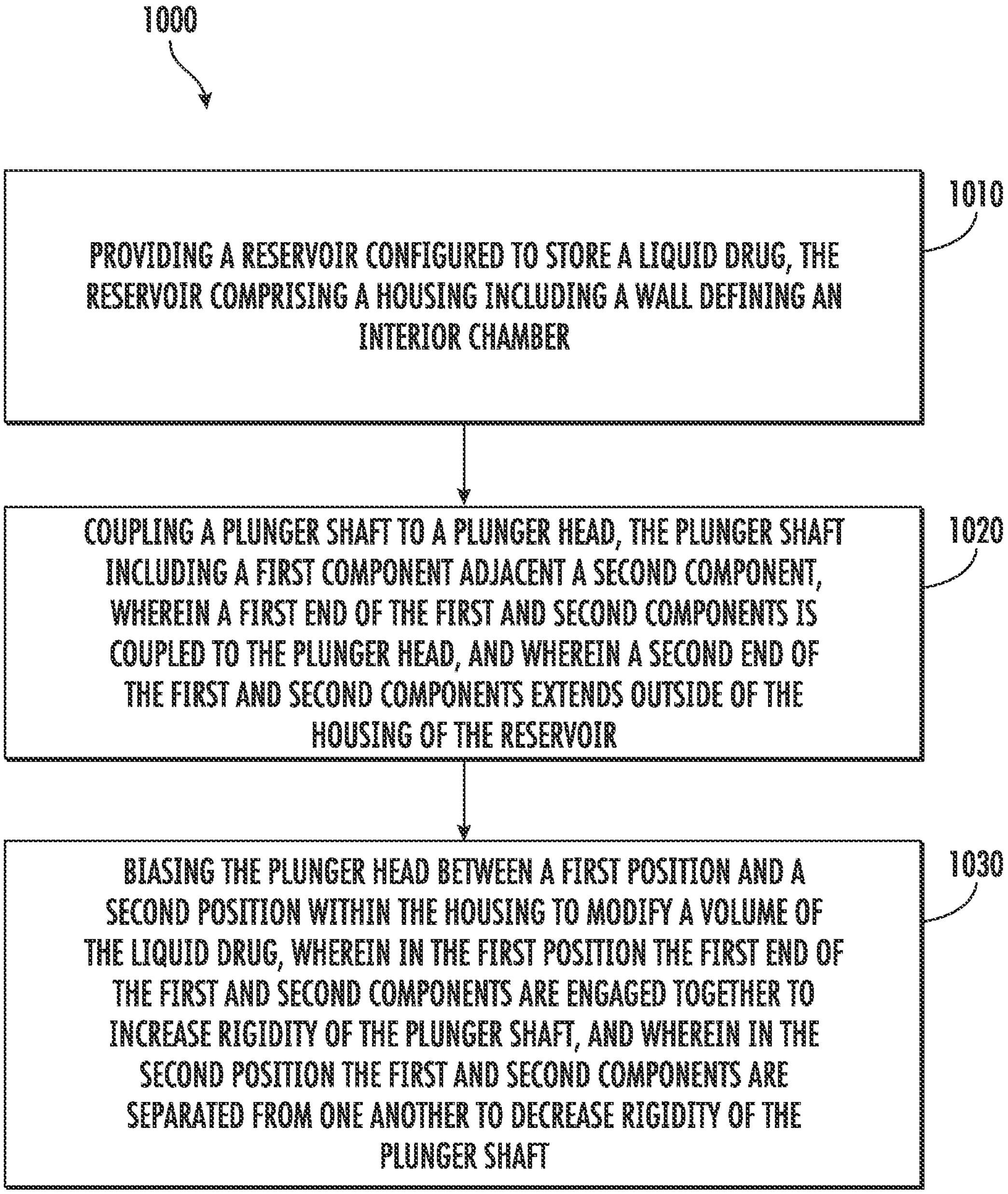
FIG. 10 illustrates a process flow of a method according to embodiments of the present disclosure.

FIG. 10 illustrates an example process 1000 according to embodiments of the present disclosure. At block 1010, the process 1000 may include providing a reservoir configured to store a liquid drug, the reservoir comprising a housing including a wall defining an interior chamber.

At block 1020, the process 1000 may include coupling a plunger shaft to a plunger head, the plunger shaft including a first component adjacent a second component, wherein a first end of the first and second components is coupled to the plunger head, and wherein a second end of the first and second components extends outside of the housing of the reservoir.

At block 1030, the process 1000 may include biasing the plunger head between a first position and a second position within the housing to modify a volume of the liquid drug, wherein in the first position the first end of the first and second components are engaged together to increase rigidity of the plunger shaft, and wherein in the second position the first and second components are separated from one another to decrease rigidity of the plunger shaft. In some embodiments, engaging the first and second components together includes interlocking a plurality of protrusions of the first component with a corresponding plurality of indentations or openings of the second component. Similarly, a plurality of protrusions of the second component may interlock with a corresponding plurality of indentations or openings of the first component. In some embodiments, the first and second components are transitioned between an unstressed rigid state and a stressed coiled state as the plunger head is biased between the first position and the second position. In some embodiments, the first and second components are coupled to one or more drive devices, wherein rotation of the one or more drive devices biases the first and second components.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 100 or any components thereof) may be implemented in hardware, software, or any combination thereof. Any component as described herein may be implemented in hardware, software, or any combination thereof. For example, the system 100 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:

a reservoir configured to store a fluid, the reservoir comprising a housing defining an interior chamber;

a drive device for driving the fluid from the reservoir, the drive device comprising:

a plunger head within the interior chamber of the housing; and a plunger shaft extending from the plunger head, wherein the plunger shaft comprises a first component adjacent a second component, each of the first component and the second component having a metal tape measure blade-like curved profile with both a top edge and a bottom edge bent away from a crest formed in a middle of the curved profile, and wherein during movement of the plunger head in a first direction the first and second components engage one another to form a rigid portion of the plunger shaft.

2. The wearable drug delivery device of claim 1, wherein the first component comprises a first plurality of protrusions and a first plurality of indentations, wherein the second component comprises a second plurality of protrusions and a second plurality of indentations, wherein the first plurality of protrusions are operable to engage the second plurality of indentations, and wherein the second plurality of protrusions are operable to engage the first plurality of indentations.

3. The wearable drug delivery device of claim 2, further comprising a first drive device engaged with the first component and a second drive device engaged with the second component, wherein the first and second drive devices are rotatable to advance and retract the first and second components relative to the housing of the reservoir.

4. The wearable drug delivery device of claim 3, wherein the first drive device comprises a first plurality of teeth operable to extend into a first plurality of openings of the first component, and wherein the second drive device comprises a second plurality of teeth operable to extend into a second plurality of openings of the second component.

5. The wearable drug delivery device of claim 1, wherein the first component is a strip of material having a first crest, wherein the second component is a strip of material having a second crest, and wherein the first and second crests engage one another to form the rigid portion of the plunger shaft.

6. The wearable drug delivery device of claim 1, wherein the first component has a first bend resistance in a first direction and a second bend resistance in a second direction, and wherein the first bend resistance in the first direction is less than the second bend resistance in the second direction.

7. The wearable drug delivery device of claim 6, wherein the second component has a first bend resistance in the first direction and a second bend resistance in the second direction, and wherein the first bend resistance in the first direction is greater than the second bend resistance in the second direction.

8. The wearable drug delivery device of claim 1, wherein the first and second components each include a first end opposite a second end, wherein the first end is coupled to the plunger head, and wherein the second end extends along an exterior of the housing of the reservoir.

9. A drive device of a wearable drug delivery device, the drive device comprising:

a plunger head in contact with an interior surface of a housing of a reservoir, the reservoir configured to store a fluid; and a plunger shaft extending from the plunger head, wherein the plunger shaft comprises a first component adjacent a second component, each of the first component and the second component having a metal tape measure blade-like curved profile with both a top edge and a bottom edge bent away from a crest formed in a middle of the curved profile, and wherein during movement of the plunger head in a first direction the first and second components engage with one another to form a rigid portion of the plunger shaft, and wherein during movement of the plunger head in a second direction, opposite the first direction, the first and second components are moved away from one another.

10. The drive device of claim 9, wherein the first component comprises a first plurality of protrusions and a first plurality of indentations, wherein the second component comprises a second plurality of protrusions and a second plurality of indentations, wherein the first plurality of protrusions are operable to interlock with the second plurality of indentations, and wherein the second plurality of protrusions are operable to interlock with the first plurality of indentations.

11. The drive device of claim 9, wherein the first component has a first crest, wherein the second component has a second crest, and wherein the first and second crests interlock with one another to form the rigid portion of the plunger shaft.

12. The drive device of claim 9, wherein the first component has a first bend resistance in a first direction and a second bend resistance in a second direction, wherein the first bend resistance of the first component in the first direction is less than the second bend resistance of the first component in the second direction, wherein the second component has a first bend resistance in the first direction and a second bend resistance in the second direction, and wherein the first bend resistance of the second component in the first direction is greater than the second bend resistance of the second component in the second direction.

13. The drive device of claim 9, further comprising a first pinion engaged with the first component and a second pinion engaged with the second component, wherein the first and second pinions are rotatable to advance and retract the first and second components relative to the housing of the reservoir.

* * * * *